(12) United States Patent
Reisfeld et al.

(10) Patent No.: US 7,803,118 B2
(45) Date of Patent: Sep. 28, 2010

(54) DETECTION OF HEART FAILURE USING A PHOTOPLETHYSMOGRAPH

(75) Inventors: Daniel Reisfeld, Tel Aviv (IL); Hila Sberro, Tel Aviv (IL)

(73) Assignee: Widemed Ltd., Herzlia (IL)

( * ) Notice: Subject to any disclaimer, the term of this patent is extended or adjusted under 35 U.S.C. 154(b) by 0 days.

(21) Appl. No.: 11/750,222

(22) Filed: May 17, 2007

(65) Prior Publication Data

US 2007/0213621 A1 Sep. 13, 2007

Related U.S. Application Data

(63) Continuation-in-part of application No. PCT/IL2006/000148, filed on Feb. 7, 2006, and a continuation-in-part of application No. PCT/IL2005/001233, filed on Nov. 22, 2005, which is a continuation of application No. 10/995,817, filed on Nov. 22, 2004, now Pat. No. 7,578,793.

(60) Provisional application No. 60/651,295, filed on Feb. 7, 2005, provisional application No. 60/843,107, filed on Sep. 7, 2006.

(51) Int. Cl.
*A61B 5/02* (2006.01)
*A61B 5/08* (2006.01)

(52) U.S. Cl. .................. 600/483; 600/484; 600/481; 600/529

(58) Field of Classification Search ......... 600/529–543, 600/473–481, 483, 484, 500–504, 323, 324, 600/326

See application file for complete search history.

(56) References Cited

U.S. PATENT DOCUMENTS

| 3,835,837 | A | 9/1974 | Peck |
| 3,863,625 | A | 2/1975 | Viglione et al. |
| 4,258,719 | A | 3/1981 | Lewyn |
| 4,545,387 | A | 10/1985 | Balique |
| 4,589,420 | A | 5/1986 | Adams et al. |
| 4,777,962 | A | 10/1988 | Watson et al. |
| 4,955,379 | A | 9/1990 | Hall |
| 5,101,831 | A | 4/1992 | Koyama et al. |
| 5,187,657 | A | 2/1993 | Forbes |
| 5,271,411 | A | 12/1993 | Ripley et al. |
| 5,280,791 | A | 1/1994 | Lavie |
| 5,385,144 | A | 1/1995 | Yamanishi et al. |
| 5,513,644 | A | 5/1996 | McClure et al. |

(Continued)

FOREIGN PATENT DOCUMENTS

WO  WO 96/16591  6/1996

(Continued)

OTHER PUBLICATIONS

Lempel et al., "A Universal Algorithm for Sequential Data Compression", IEEE Transactions on Information Theory, IT-23:3 (1977), pp. 337-349.

(Continued)

*Primary Examiner*—Charles A. Marmor, II
*Assistant Examiner*—Navin Natnithithadha

(57) ABSTRACT

A method for diagnosis includes receiving a signal associated with blood oxygen saturation of a patient during sleep. The signal is filtered so as to eliminate signal components at frequencies equal to and greater than a respiratory frequency of the patient. The filtered signal is processed to detect a pattern corresponding to multiple cycles of periodic breathing.

74 Claims, 7 Drawing Sheets

U.S. PATENT DOCUMENTS

| | | | |
|---|---|---|---|
| 5,560,369 A | 10/1996 | McClure et al. | |
| 5,588,425 A | 12/1996 | Sackner et al. | |
| 5,605,151 A | 2/1997 | Lynn | |
| 5,605,158 A | 2/1997 | Snell | |
| 5,623,933 A | 4/1997 | Amano et al. | |
| 5,685,315 A | 11/1997 | McClure et al. | |
| 5,718,242 A | 2/1998 | McClure et al. | |
| 5,720,294 A | 2/1998 | Skinner | |
| 5,755,229 A | 5/1998 | Amano et al. | |
| 5,769,825 A | 6/1998 | Lynn | |
| 5,803,066 A | 9/1998 | Rapoport et al. | |
| 5,819,007 A | 10/1998 | Elghazzawi | |
| 5,846,208 A | 12/1998 | Pichlmayr et al. | |
| 5,857,978 A | 1/1999 | Hively et al. | |
| 5,865,756 A | 2/1999 | Peel, III | |
| 5,891,023 A | 4/1999 | Lynn | |
| 5,902,250 A | 5/1999 | Verrier et al. | |
| 5,999,846 A | 12/1999 | Pardey et al. | |
| 6,011,477 A | 1/2000 | Teodorescu | |
| 6,032,072 A | 2/2000 | Greenwald et al. | |
| 6,070,098 A | 5/2000 | Moore-Ede et al. | |
| 6,095,984 A | 8/2000 | Amano et al. | |
| 6,122,536 A | 9/2000 | Sun et al. | |
| 6,142,950 A | 11/2000 | Allen et al. | |
| 6,223,064 B1 | 4/2001 | Lynn et al. | |
| 6,304,775 B1 | 10/2001 | Iasemidis et al. | |
| 6,308,094 B1 | 10/2001 | Shusterman et al. | |
| 6,319,205 B1 | 11/2001 | Goor et al. | |
| 6,322,515 B1 | 11/2001 | Goor et al. | |
| 6,342,039 B1 * | 1/2002 | Lynn et al. | 600/529 |
| 6,361,501 B1 | 3/2002 | Amano et al. | |
| 6,375,623 B1 | 4/2002 | Gavriely | |
| 6,409,675 B1 * | 6/2002 | Turcott | 600/508 |
| 6,480,733 B1 * | 11/2002 | Turcott | 600/516 |
| 6,480,734 B1 | 11/2002 | Zhang et al. | |
| 6,511,424 B1 | 1/2003 | Moore-Ede et al. | |
| 6,519,490 B1 | 2/2003 | Wiesel | |
| 6,527,729 B1 * | 3/2003 | Turcott | 600/528 |
| 6,529,752 B2 * | 3/2003 | Krausman et al. | 600/323 |
| 6,549,804 B1 | 4/2003 | Osorio et al. | |
| 6,589,188 B1 | 7/2003 | Street et al. | |
| 6,595,929 B2 | 7/2003 | Stivoric et al. | |
| 6,600,949 B1 | 7/2003 | Turcott | |
| 6,608,562 B1 | 8/2003 | Kimura et al. | |
| 6,609,016 B1 | 8/2003 | Lynn | |
| 6,702,752 B2 | 3/2004 | Dekker | |
| 6,748,252 B2 | 6/2004 | Lynn et al. | |
| 6,752,765 B1 | 6/2004 | Strobel et al. | |
| 6,760,608 B2 | 7/2004 | Lynn | |
| 6,805,673 B2 | 10/2004 | Dekker | |
| 6,829,501 B2 | 12/2004 | Nielsen et al. | |
| 6,839,581 B1 | 1/2005 | El-Solh et al. | |
| 6,856,829 B2 | 2/2005 | Ohsaki et al. | |
| 6,878,121 B2 | 4/2005 | Krausman et al. | |
| 6,881,192 B1 | 4/2005 | Park | |
| 7,001,337 B2 | 2/2006 | Dekker | |
| 7,020,514 B1 | 3/2006 | Wiesel | |
| 7,024,233 B2 | 4/2006 | Ali et al. | |
| 7,024,234 B2 | 4/2006 | Margulies et al. | |
| 7,039,538 B2 | 5/2006 | Baker, Jr. | |
| 7,070,568 B1 * | 7/2006 | Koh | 600/508 |
| 7,081,095 B2 | 7/2006 | Lynn et al. | |
| 7,082,329 B2 | 7/2006 | Järverud | |
| 7,160,252 B2 * | 1/2007 | Cho et al. | 600/323 |
| 7,177,686 B1 * | 2/2007 | Turcott | 607/23 |
| 7,190,261 B2 | 3/2007 | Al Ali | |
| 7,225,013 B2 | 5/2007 | Geva et al. | |
| 7,314,451 B2 * | 1/2008 | Halperin et al. | 600/534 |
| 7,324,845 B2 | 1/2008 | Mietus et al. | |
| 7,343,198 B2 | 3/2008 | Behbehani et al. | |
| 7,351,206 B2 | 4/2008 | Suzuki et al. | |
| 7,357,775 B1 * | 4/2008 | Koh | 600/536 |
| 7,386,340 B2 | 6/2008 | Schlegel et al. | |
| 7,396,333 B2 | 7/2008 | Stahmann et al. | |
| 7,398,115 B2 | 7/2008 | Lynn | |
| 7,413,549 B1 | 8/2008 | Koh | |
| 7,438,686 B2 * | 10/2008 | Cho et al. | 600/484 |
| 7,468,040 B2 | 12/2008 | Hartley et al. | |
| 7,479,114 B2 | 1/2009 | Hartley et al. | |
| 7,510,531 B2 | 3/2009 | Lee et al. | |
| 7,640,055 B2 | 12/2009 | Geva et al. | |
| 7,674,230 B2 | 3/2010 | Reisfeld | |
| 2001/0018557 A1 | 8/2001 | Lynn et al. | |
| 2002/0002327 A1 * | 1/2002 | Grant et al. | 600/324 |
| 2002/0007124 A1 | 1/2002 | Woodward | |
| 2002/0095076 A1 * | 7/2002 | Krausman et al. | 600/323 |
| 2002/0138013 A1 | 9/2002 | Guerrero et al. | |
| 2002/0173707 A1 | 11/2002 | Lynn et al. | |
| 2002/0190863 A1 | 12/2002 | Lynn | |
| 2003/0000522 A1 | 1/2003 | Lynn et al. | |
| 2003/0004423 A1 | 1/2003 | Lavie et al. | |
| 2003/0004652 A1 | 1/2003 | Brunner et al. | |
| 2003/0055351 A1 | 3/2003 | Wiesel | |
| 2003/0120164 A1 | 6/2003 | Nielsen et al. | |
| 2003/0144597 A1 | 7/2003 | Bock | |
| 2003/0158466 A1 | 8/2003 | Lynn et al. | |
| 2004/0039292 A1 | 2/2004 | Schlegel et al. | |
| 2004/0059236 A1 | 3/2004 | Margulies et al. | |
| 2004/0068199 A1 | 4/2004 | Echauz et al. | |
| 2004/0073098 A1 | 4/2004 | Geva et al. | |
| 2004/0193068 A1 | 9/2004 | Burton et al. | |
| 2004/0230105 A1 | 11/2004 | Geva et al. | |
| 2005/0062609 A9 | 3/2005 | Lynn | |
| 2005/0076908 A1 | 4/2005 | Lee et al. | |
| 2005/0080349 A1 | 4/2005 | Okada et al. | |
| 2005/0148893 A1 | 7/2005 | Misczynski et al. | |
| 2005/0192508 A1 | 9/2005 | Lange et al. | |
| 2005/0240091 A1 | 10/2005 | Lynn | |
| 2006/0041201 A1 | 2/2006 | Behbehani et al. | |
| 2006/0111635 A1 * | 5/2006 | Todros et al. | 600/484 |
| 2006/0149144 A1 | 7/2006 | Lynn et al. | |
| 2006/0155206 A1 | 7/2006 | Lynn | |
| 2006/0155207 A1 | 7/2006 | Lynn et al. | |
| 2006/0161071 A1 | 7/2006 | Lynn et al. | |
| 2006/0189880 A1 | 8/2006 | Lynn et al. | |
| 2006/0195037 A1 | 8/2006 | Wiesel | |
| 2006/0195041 A1 | 8/2006 | Lynn et al. | |
| 2006/0235324 A1 | 10/2006 | Lynn | |
| 2006/0276695 A9 | 12/2006 | Lynn et al. | |
| 2006/0293602 A1 | 12/2006 | Clark | |
| 2007/0016095 A1 | 1/2007 | Low et al. | |
| 2007/0021979 A1 | 1/2007 | Cosentino et al. | |
| 2007/0093721 A1 | 4/2007 | Lynn et al. | |
| 2007/0118054 A1 | 5/2007 | Pinhas et al. | |
| 2007/0129647 A1 | 6/2007 | Lynn | |
| 2007/0149860 A1 | 6/2007 | Lynn et al. | |
| 2007/0149870 A1 | 6/2007 | Rosenthal | |
| 2007/0167843 A1 * | 7/2007 | Cho et al. | 600/484 |
| 2007/0191688 A1 | 8/2007 | Lynn | |
| 2007/0191697 A1 | 8/2007 | Lynn et al. | |
| 2007/0208269 A1 | 9/2007 | Mumford et al. | |
| 2007/0213620 A1 | 9/2007 | Reisfeld | |
| 2007/0213621 A1 | 9/2007 | Reisfeld et al. | |
| 2007/0213622 A1 | 9/2007 | Reisfeld | |
| 2007/0213624 A1 | 9/2007 | Reisfeld et al. | |
| 2007/0239057 A1 | 10/2007 | Pu et al. | |
| 2007/0244408 A1 | 10/2007 | Wingeier et al. | |
| 2008/0177195 A1 | 7/2008 | Armistead | |
| 2008/0200775 A1 | 8/2008 | Lynn | |
| 2008/0200819 A1 | 8/2008 | Lynn et al. | |
| 2008/0269583 A1 | 10/2008 | Reisfeld | |
| 2008/0287756 A1 | 11/2008 | Lynn | |
| 2008/0300500 A1 | 12/2008 | Reisfeld | |
| 2008/0312166 A1 | 12/2008 | Lynn et al. | |

| | | | |
|---|---|---|---|
| 2009/0281838 | A1 | 11/2009 | Lynn et al. |
| 2009/0281839 | A1 | 11/2009 | Lynn et al. |
| 2009/0292478 | A1 | 11/2009 | Avinash et al. |
| 2009/0299150 | A1 | 12/2009 | Alberte, Jr. et al. |
| 2009/0306482 | A1 | 12/2009 | Davis et al. |
| 2009/0312612 | A1 | 12/2009 | Rantala |

FOREIGN PATENT DOCUMENTS

| | | |
|---|---|---|
| WO | WO 00/10455 | 3/2000 |
| WO | WO 03/057025 | 7/2003 |
| WO | WO 2004/075746 | 9/2004 |
| WO | WO 2006/008743 | 1/2006 |
| WO | WO 2006/054306 | 5/2006 |
| WO | WO 2006/082589 | 8/2006 |
| WO | WO 2008/029399 | 3/2008 |
| WO | WO 2009/137682 | 11/2009 |

OTHER PUBLICATIONS

Akselrod et al., "Power Spectrum Analysis of Heart Rate Fluctuation: A Quantitative Probe of Beat-to-Beat Cardiovascular Control", Science 213 (1981), pp. 220-222.

Eamonn Keogh, et al., "An Online Algorithm for Segmenting Time Series", pp. 289-296, 2001.

Penzel, et al, "Computer Based Sleep Recording and Analysis", Sleep Medicine Reviews 4:2 (2000), pp. 131-148.

Tesler, et al, "Can One Detect Sleep Stage Transitions for On-Line Sleep Scoring by Monitoring the Heart Rate Variability?" Somnologie 8 (2004), pp. 33-41.

A.K. Jain, et al, "Data Clustering: A Review", ACM Computing Surveys, vol. 31, No. 3, Sep. 1999.

http://www.sleepdisorderchannel.net, 2004.

M.G. Terzano, et al, "Atlas, rules, and recording techniques for the scoring of cyclic alternating pattern (CAP) in human sleep", Sleep Medicine 2 (2001), pp. 537-553.

T.D. Bradley, et al., "Sleep apnea and heart failure", Circulation 2003; 107:1671-1678.

J.L. Peppin, et al., "Cheyne stokes respiration with central sleep apnoea in chronic heart failure: proposals for a diagnostic and therapeutic strategy", Sleep medicine reviews (2006) 10, 33-47.

U. Cora, et al., "Sleep and exertional periodic breathing in chronic heart failure", Circulation 2006; 113:44-50.

T. Penzel, et al., "Systematic comparison of different algorithms for apnoea detection based on electronic recordings", Med. Biol. Eng. Comput., 2002, 40, 402-407.

H.W. Duchna, et al., "Sleep-disordered breathing and cardio and cerebrovascular diseases: 2003 update of clinical significance and future perspectives", Somnlogie 7: 101-121, 2003.

M. Folke, et al., "Critical review of non-invasive respiratory monitoring in medical care", Medical & Biol Eng & Comp 2003, vol. 41.

U.S. Appl. No. 60/651,295.

"Heart rate variability", European Heart Journal 1996, 17, 354-381.

J.J. Verbeek, et al., "Efficient greedy learning of Gaussian mixture models", Neural Computation, 5(2): 469-485, Feb. 2003.

L.R. Rabiner, "A tutorial on hidden markov models and selected applications in speech recognition", Proc. of the IEEE, vol. 77, No. 2, Feb. 1989.

P. Jourdain, et al., "Plasma brain natriuretic peptide-guided therapy to improve outcome in heart failure: the STARS-BNP multicenter study", JACC vol. 49, No. 16, 2007.

"Sleep related breathing disorders in adults: recommendations for syndrome definition and measurement techniques in clinical research", Sleep, vol. 22, No. 5, 1999.

G.A. Wright, et al., "Natriuretic peptides as a prognostic marker and therapeutic target in heart failure", Heart 2006; 92:149-151.

W. Rosamond, et al., "Heart disease and stroke statistics—2007 update: A report from the American heart association statistics committee and stroke statistics subcommittee", Circulation Feb. 6, 2007.

C.A. Kushhida, et al., "Practice parameters for the indications for polysomnography and related procedures: an update for 2005", Sleep vol. 28, No. 4, 2005.

G. Tusman, et al., "Effect of pulmonary perfusion on the slopes of single-breath test of CO2", J Appl Physiol 99:650-655, 2005.

International Preliminary Report on Patentability Dated Apr. 16, 2009 From the International Bureau of WIPO Re.: Application No. PCT/IL2007/001092.

International Search Report Dated Jul. 22, 2008 From the International Searching Authority Re.: Application No. PCT/IL07/01092.

Notice of Allowance Dated Feb. 2, 2007 From the US Patent and Trademark Office Re.: No. U.S. Appl. No. 10/678,773.

Notice of Allowance Dated Sep. 3, 2009 From the US Patent and Trademark Office Re.: U.S. Appl. No. 10/677,176.

Notice of Allowance Dated Nov. 9, 2009 From the US Patent and Trademark Office Re.: U.S. Appl. No. 11/750,221.

Notice of Allowance Dated Apr. 15, 2009 From the US Patent and Trademark Office Re.: U.S. Appl. No. 10/995,817.

Official Action Dated Oct. 1, 2008 From the US Patent and Trademark Office Re.: U.S Appl. No. 10/677,176.

Official Action Dated Apr. 3, 2009 From the US Patent and Trademark Office Re.: U.S. Appl. No. 10/677,176.

Official Action Dated Sep. 3, 2009 From the US Patent and Trademark Office Re.: U.S. Appl. No. 11/750,173.

Official Action Dated Feb. 5, 2009 From the US Patent and Trademark Office Re.: U.S. Appl. No. 11/750,173.

Official Action Dated Feb. 5, 2009 From the US Patent and Trademark Office Re.: U.S. Appl. No. 11/750,250.

Official Action Dated Jun. 6, 2008 From the US Patent and Trademark Office Re.: U.S. Appl. No. 10/677,176.

Official Action Dated Oct. 8, 2009 From the US Patent and Trademark Office re.: U.S. Appl. No. 10/677,176.

Official Action Dated Mar. 9, 2009 From the US Patent and Trademark Office Re.: U.S. Appl. No. 11/750,221.

Official Action Dated Sep. 9, 2008 From the US Patent and Trademark Office Re.: U.S. Appl. No. 11/750,221.

Official Action Dated Aug. 13, 2008 From the US Patent and Trademark Office Re.: U.S. Appl. No. 11/750,173.

Official Action Dated May 14, 2008 From the US Patent and Trademark Office Re.: U.S. Appl. No. 10/995,817.

Official Action Dated Oct. 14, 2009 From the US Patent and Trademark Office Re.: U.S. Appl. No. 11/750,250.

Official Action Dated Aug. 15, 2008 From the US Patent and Trademark Office Re.: U.S. App. No. 11/750,250.

Official Action Dated Jan. 21, 2009 From the US Patent and Trademark Office Re.: U.S. Appl. No. 10/995,817.

Official Action Dated Jul. 22, 2009 From the US Patent and Trademark Office Re.: U.S. Appl. No. 11/750,221.

Official Action Dated Jan. 23, 2008 From the US Patent and Trademark Office Re.: U.S. Appl. No. 10/995,817.

Official Action Dated Jul. 31, 2008 From the US Patent and Trademark Office Re.: U.S. Appl. No. 10/995,817.

Response Dated Jun. 1, 2009 to Official Action of Feb. 5, 2009 From the US Patent and Trademark Office Re.: U.S. Appl. No. 11/750,173.

Response Dated Jun. 2, 2009 to Official Action of Feb. 5, 2009 From the US Patent and Trademark Office Re.: U.S. Appl. No. 11/750,250.

Response Dated Jun. 3, 2009 to Official Action of Apr. 3, 2009 From the US Patent and Trademark Office Re.: U.S. Appl. No. 10/677,176.

Response Dated Mar. 13, 2009 to Official Action of Jan. 21, 2009 From the US Patent and Trademark Office Re.: U.S. Appl. No. 10/995,817.

Response Dated Oct. 17, 2008 to Official Action of Jul. 31, 2008 From the US Patent and Trademark Office Re.: U.S. Appl. No. 10/995,817.

Response Dated Feb. 19, 2008 to Official Action of Jan. 23, 2008 From the US Patent and Trademark Office Re.: U.S. Appl. No. 10/995,817.

Response Dated May 21, 2008 to Official Action of May 14, 2008 From the US Patent and Trademark Office Re.: U.S. Appl. No. 10/995,817.

Response Dated Oct. 24, 2008 to Official Action of Aug. 13, 2008 From the US Patent and Trademark Office Re.: U.S. Appl. No. 11/750,173.

Response Dated Oct. 24, 2008 to Official Action of Aug. 15, 2008 From the US Patent and Trademark Office Re.: U.S. Appl. No. 11/750,250.

Response Dated Dec. 28, 2008 to Official Action of Oct. 1, 2008 From the US Patent and Trademark Office Re.: U.S. Appl. No. 10/677,176.

Supplementary European Search Report and the European Search Opinion Dated Feb. 2, 2009 From the European Patent Office Re.: Application No. 05761327.5.

Supplementary European Search Report and the European Search Opinion Dated Oct. 8, 2009 From the European Patent Office Re.: Application No. 06704643.3.

Written Opinion Dated Jul. 22, 2008 From the International Searching Authority Re.: Application No. PCT/IL07/01092.

Agarwal et al. "Automatic EEG Analysis During Long-Term Monitoring in the ICU", Electroencephalography and Clinical Neurophysiology, XP002510061, 107(1): 44-58, Jul. 1998. p. 45, r-h col., Line 25—p. 50, 1-h col., Line 5, p. 50, 1-h col., Line 29—p. 51, r-h col., Line 24, p. 54, r-h col., Line 32—p.55, r-h col., Line 21.

Agarwal et al. "Computer-Assisted Sleep Staging Based on Segmentation and Clustering", Proceedings of 23rd Annual International Conference of the IEEE Engineering in Medicine and Biology Society, 2001 Conference Proceedings (EMBS), Istanbul, Turkey, Oct. 25-28, 2001, XP010594756, 2: 1695-1698, Oct. 25, 2001. p. 1695, r-h col., Line 27—p. 1697, 1-h col., Line 36.

Agarwal et al. "Computer-Assisted Sleep Staging", IEEE Transactions on Biomedical Engineering, XP011007173, 48(12): 1412-1423, Dec. 1, 2001. p. 1413, 1-h col., Line 26—p. 1418, r-h col., Line 14.

Akselrod et al. "Power Spectrum Analysis of Heart Rate Fluctuation: A Quantitative Prode of Beat-to-Beat Cardiovascular Control", Science, 213: 220-222, Jul. 10, 1981.

Bodenstein et al. "Feature Extraction From the Electroencephalogram by Adaptive Segmentation", Proceedings of the IEEE, 65(5): 642-652, May 1977.

Gath et al. "Unsupervised Optimal Fuzzy Clustering", IEEE Transactions on Pattern Analysis and Machine Intelligence, 11(7): 773-781, Jul. 1989.

Geva et al. "Forecasting Generalized Epileptic Seizures From the EEG Signal by Wavelet Analysis ans Dynamic Unsupervised Fuzzy Clustering", IEEE Transactions on Biomedical Engineering, 45(10): 1205, Oct. 1998. Abstract.

Healthcommunities "Sleep Stages", Sleepchannel.com, Retrieved From the Internet: http://www.sleepdisorderchannel.net/stages, 2004.

Hutt et al. "Analysis and Modeling of Quasi-Stationary Multivariate Time Series and Their Application to Middle Latency Auditory Evoked Potentials", Physica D, XP002510063, 177(1-4): 203-232, Mar. 15, 2003.

Jain et al. "Data Clustering: A Review", ACM Computing Surveys, 31(3): 264-323, Sep. 1999.

Kaplan et al. "Macrostructural EEG Characterization Based on Nonparametric Change Point Segmentation: Application to Sleep Analysis", Journal of Neurscience Methods, XP002510060, 106(1): 81-90, Mar. 30, 2001. p. 83, r-h col., Line 30—p. 86, 1-h col., Line 2, p. 86, r-h col., Lines 18-54, p. 88, 1-h col., Line 2—p. 90, 1-h col., Line 38.

Keogh et al. "An Online Algorithm for Segmenting Time Series", Proceedings of the 2001 IEEE International Conference on Data-Mining, ICDM, p. 289-296, 2001.

Klösch et al. "The SIESTA Project Polygraphic and Clinical Database. A New Approach to Studying Subjective and Objective Measurements of Human Sleep", IEEE Engineering in Medicine and Biology Magazine: The Quarterly Magazine of the Engineering in Medicine & Biology Society, XP002510064, 20(3): 51-57, May 2001.

Lempel et al. "A Universal Algorithm for Sequential Data Compression", IEEE Transactions on Information Theory, 23(3): 337-349, May 1977.

Malik et al. "Heart Rate Variability. Standards of Measurement, Physiological Interpretation, and Clinical Use", European Heart Journal, 17: 354-381, 1996.

Murphy "Hidden Markov Model (HMM) Toolbox for Matlab", 1 P., 1998. Retrieved From the Internet: http://www.cs.ubc.ca/~murphyk/Software/HMM/hmm.mtl.

Paul et al. "Comparison of Quantitative EEG Characteristics of Quiet and Active Sleep in Newborns", Sleep Medicine, XP002510062, 4(6): 543-552, Nov. 2003. p. 544, r-h col., Line 21—p.548, 1-h col., Line 38.

Penzel et al. "Computer Based Sleep Recording and Analysis", Sleep Medicine Review, 4(2): 131-148, 2000.

Penzel et al. "Systematic Comparison of Different Algorithms for Apnoea Detection Based on Electrocardiogram Recordings", Medical & Biological Engineering & Computing, 40: 402-407, 2002.

Pépin et al. "Cheyne Stokes Respiration With Central Sleep Apnoea in Chronic Heart Failure: Proposals for A Diagnostic and Therapeutic Strategy", Sleep Medicine Reviews, 10(1): 33-47, 2006.

Roberts et al. "New Method of Automated Sleep Quantification", Medical & Biological Engineering & Computing, 30: 509-517, Sep. 1992.

Sackellares et al. "Epilepsy—When Chaos Fails in Chaos in the Brain", Eds, 1999.

Telser et al. "Can One Detect Sleep Stage Transitions for On-Line Sleep Scoring by Monitoring the Heat Rate Variability?", Somnologie, 8: 33-41, 2004.

Terzano et al. "Atlas, Rules, and Recording Techniques for the Scoring of Cyclic Alternating Pattern (CAP) in Human Sleep", Sleep Medicine, 2: 537-553, 2001.

Tusman et al. "Effect of Pulmonary Perfusion on the Slopes of Single-Breath Test of CO2", Journal of Applied Physiology, 99(2): 650-655, 2005.

Verbeek et al. "Efficient Greedy Learning of Gaussian Mixture Models", Neural Computation, 15(2): 469-485, Feb. 2003.

Xu-Sheng et al. "EEG Complexity As A Measure of Depth of Anesthesia for Patients", IEEE Transactions on Biomedical Engineering, 48(12):1424-1433, Dec. 2001. Abstract.

Ziv et al. "A Universal Algorithm for Sequential Data Compression", IEEE Transactions on Information Theory, IT-23(3): 337-343, May 1977.

Communication Pursuant to Article 94(3) EPC Dated Feb. 8, 2010 From the European Patent Office Re.: Application No. 05808274.4.

Response Dated Jan. 4, 2010 to Official Action of Sep. 3, 2009 From the US Patent and Trademark Office Re.: U.S. Appl. No. 11/750,173.

Supplementary European Search Report and the European Search Opinion Dated Nov. 3, 2009 From the European Patent Office Re.: Application No. 05808274.4.

Covidien "Covidien Launches Alarm Management Systm for the Nellcor(™) OxiMax(™) N-600x(™) Pulse Oximeter", Covidien Bussiness Wire, Apr. 16, 2009.

Redmond et al. "Electrocardiogram-Based Automatic Sleep Staging in Sleep Disordered Breathing", Computers in Cardiology, XP010698978, 30: 609-612, Sep. 21, 2003. Section 3, Feature Extraction, Section 5, Subject Specific Calssification, Section 6, Subject Independant Classification.

Watanabe et al. "Estmation of Sleep Stages Based on Heart Rate Fluctuation and Body Movement", SICE 2004 Annual Conference, IEEE, XP010824823, 3: 2153-2156, Aug.4, 2004. Section 2.2 Measurement System, Section 4.1 Indices, Figs.l, 2.

Response Dated Mar. 15, 2010 to Official Action of Oct. 14, 2009 From the US Patent and Trademark Office Re.: U.S. Appl. No. 11/750,250.

Notice of Allowance Dated May 3, 2010 From the US Patent and Trademark Office Re.: U.S. Appl. No. 11/750,173.

Response Dated Jun. 8, 2010 to Communication Pursuant to Article 94(3) EPC of Feb. 8, 2010 From the European Patent Office Re.: Application No. 05808274.4.

Office Action Dated Jun. 7, 2010 From the Israel Patent Office Re. Application No. 147502 and Its Translation Into English.

* cited by examiner

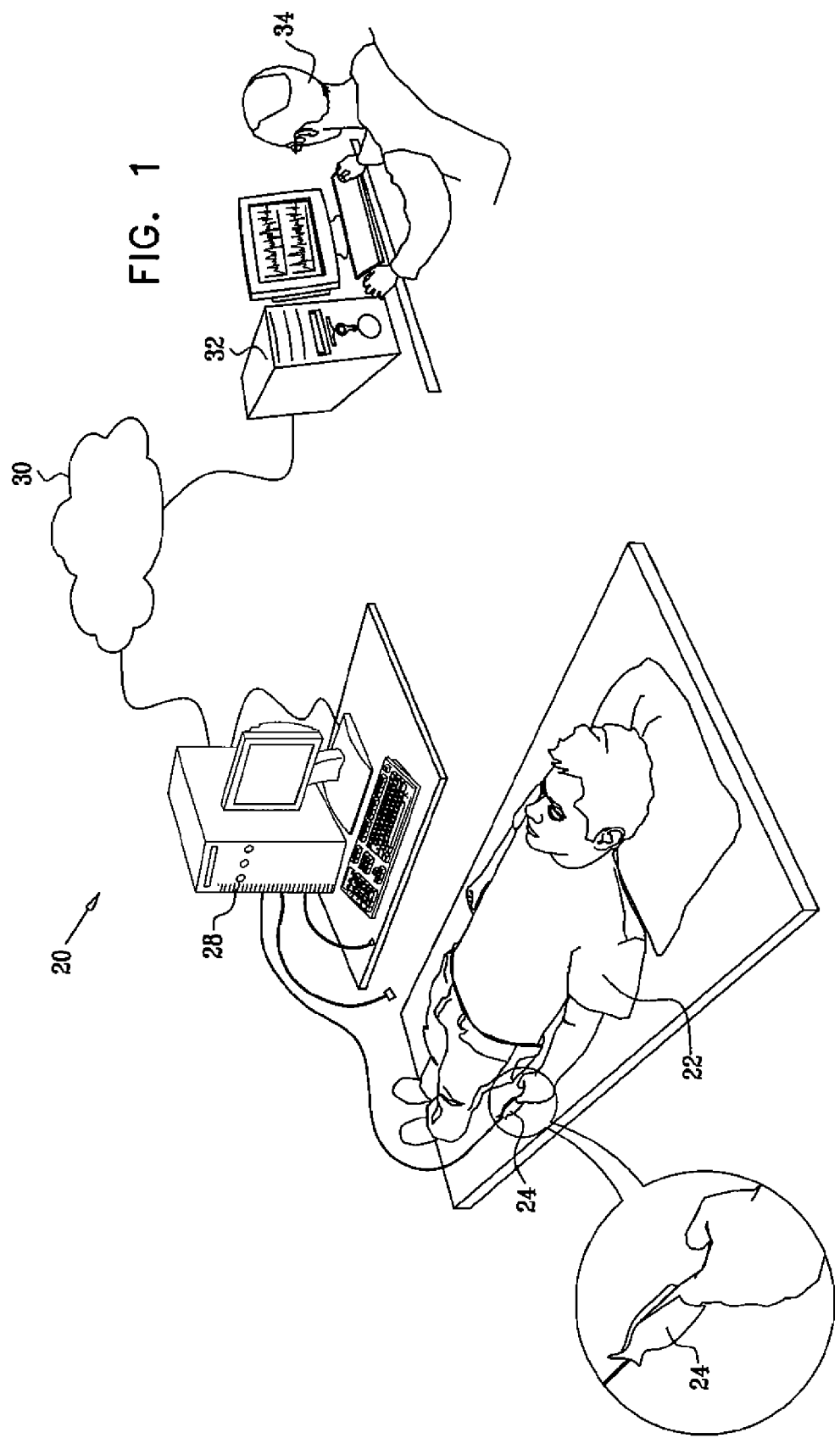

DETECTION OF HEART FAILURE USING A PHOTOPLETHYSMOGRAPH

CROSS-REFERENCE TO RELATED APPLICATIONS

This application is a Continuation-In-Part of PCT patent application PCT/IL2005/001233, filed Nov. 22, 2005, which is a Continuation of application Ser. No. 10/995,817, filed Nov. 22, 2004 and which claims the priority of U.S. Provisional Patent Application 60/843,107, filed Sep. 7, 2006, and is a Continuation-In-Part of PCT patent application PCT/IL2006/000148, filed Feb. 7, 2006, claiming the priority of U.S. Provisional Patent Application 60/651,295, filed Feb. 7, 2005. This application is related to three other U.S. patent applications, all filed on even date, which are entitled "Detection of Heart Failure Using a Photoplethysmograph," "Respiration-Based Prognosis of Heart Disease," and "Sleep Monitoring Using a Photoplethysmograph." The disclosure of all of these related applications are incorporated herein by reference.

FIELD OF THE INVENTION

The present invention relates generally to physiological monitoring and diagnosis, and specifically to sleep recording and analysis.

BACKGROUND OF THE INVENTION

Human sleep is generally described as a succession of five recurring stages (plus waking, which is sometimes classified as a sixth stage). Sleep stages are typically monitored using a polysomnograph to collect physiological signals from the sleeping subject, including brain waves (EEG), eye movements (EOG), muscle activity (EMG), heartbeat (ECG), blood oxygen levels (SpO2) and respiration. The commonly-recognized stages include:

- Stage 1 sleep, or drowsiness. The eyes are closed during Stage 1 sleep, but if aroused from it, a person may feel as if he or she has not slept.
- Stage 2 is a period of light sleep, during which the body prepares to enter deep sleep.
- Stages 3 and 4 are deep sleep stages, with Stage 4 being more intense than Stage 3.
- Stage 5, REM (rapid eye movement) sleep, is distinguishable from non-REM (NREM) sleep by changes in physiological states, including its characteristic rapid eye movements.

Polysomnograms show brain wave patterns in REM to be similar to Stage 1 sleep. In normal sleep, heart rate and respiration speed up and become erratic, while the muscles may twitch. Intense dreaming occurs during REM sleep, but paralysis occurs simultaneously in the major voluntary muscle groups.

Sleep apneas commonly occur in conjunction with a variety of cardiorespiratory disorders. The relationship between sleep apnea and heart failure, for example, is surveyed by Bradley et al. in two articles entitled "Sleep Apnea and Heart Failure," including "Part I: Obstructive Sleep Apnea," Circulation 107, pages 1671-1678 (2003), and "Part II: Central Sleep Apnea," Circulation 107, pages 1822-1826 (2003), which are incorporated herein by reference. The authors define "apnea" as a cessation of airflow for more than 10 sec. This term is distinguished from "hypopnea," which is a reduction in but not complete cessation of airflow to less than 50% of normal, usually in association with a reduction in oxyhemoglobin saturation (commonly referred to as "desaturation").

Sleep apneas and hypopneas are generally believed to fall into two categories: obstructive, due to collapse of the pharynx; and central, due to withdrawal of central respiratory drive to the muscles of respiration. Central sleep apnea (CSA) is commonly associated with Cheyne-Stokes respiration, which is a form of periodic breathing in which central apneas and hypopneas alternate with periods of hyperventilation, with a waxing-waning pattern of tidal volume. CSA is believed to arise as the result of heart failure, though obstructive sleep apnea (OSA) may also occur in heart failure patients.

Both OSA and CSA increase the strain on the cardiovascular system and thus worsen the prognosis of the heart failure patient. In some cases, both types of apneas may occur in the same patient, even at the same time (superposition). Classifying respiratory events as central or obstructive is considered to be a critical point, since treatment may differ according to the type of events, as pointed out by Pepin et al. in "Cheyne-Stokes Respiration with Central Sleep Apnea in Chronic Heart Failure: Proposals for a Diagnostic and Therapeutic Strategy," Sleep Medicine Reviews 10, pages 33-47 (2006), which is incorporated herein by reference. Both CSA and OSA can be manifested in periodic breathing patterns.

Various methods have been proposed in the patent literature for automated apnea detection and diagnosis based on patient monitoring during sleep. For example, U.S. Patent Application Publication US 2004/0230105 A1 describes a method for analyzing respiratory signals using a Fuzzy Logic Decision Algorithm (FLDA). The method may be used to associate respiratory disorders with obstructive apnea, hypopnea, central apnea, or other conditions. As another example, U.S. Patent Application Publication US 2002/0002327 A1 and U.S. Pat. No. 6,839,581 describe methods for detecting Cheyne-Stokes respiration, which may be used on patients with heart failure. The methods involve performing spectral analysis of overnight oximetry recordings, from which a classification tree is generated. Another method, based on monitoring oxygen saturation and calculating the slope of desaturation events, is described in U.S. Pat. No. 6,760,608. Yet another method for classifying sleep apneas is described in U.S. Pat. No. 6,856,829. In this case, pulse waves from the body of a patient are detected, and the envelope of the pulse waves is created by connecting every peak of the pulse waves. The normalized amplitude and period of the envelope are used in determining whether the patient has OSA, CSA, or mixed sleep apnea syndrome. The disclosures of the patents and patent applications cited above are incorporated herein by reference.

It has been suggested that sleep monitoring can be used for assessing cardiorespiratory risk. For example, U.S. Pat. No. 5,902,250, whose disclosure is incorporated herein by reference, describes a home-based, wearable, self-contained system that determines sleep-state and respiratory pattern, and assesses cardiorespiratory risk. A respiratory disorder may be diagnosed from the frequency of eyelid movements and/or from ECG signals. Cardiac disorders (such as cardiac arrhythmia or myocardial ischemia) that are known to be linked to certain respiratory disorders also may be inferred upon detection of such respiratory disorders.

Photoplethysmograph devices, known commonly as pulse oximeters, provide instantaneous in vivo measurement of arterial oxygenation by determining the color of blood between a light source and a photodetector. To determine the blood oxygen saturation, light absorption measurement is carried out at two wavelengths in the red and infrared ranges. The difference between background absorption during diastole and peak absorption during systole at both wavelengths is used to compute the blood oxygen saturation.

Photoplethysmograph signals provide information not only on blood oxygenation, but also on other physiological signs. For example, U.S. Pat. No. 5,588,425 describes the use of a pulse oximeter in validating the heart rate and/or R-R intervals of an ECG, and for discriminating between sleep and wakefulness in a monitored subject. It also describes a method for distinguishing between valid pulse waveforms in the oximeter signal. U.S. Pat. No. 7,001,337 describes a method for obtaining physiological parameter information related to respiration rate, heart rate, heart rate variability, blood volume variability and/or the autonomic nervous system using photoplethysmography. U.S. Pat. No. 7,190,261 describes an arrhythmia alarm processor, which detects short-duration, intermittent oxygen desaturations of a patient using a pulse oximeter as a sign of irregular heartbeat. An alarm is triggered when the pattern of desaturations matches a reference pattern. The disclosures of the above-mentioned patents are incorporated herein by reference.

SUMMARY OF THE INVENTION

The photoplethysmograph signals that are output by a standard pulse oximeter can provide a wealth of information regarding the patient's vital signs and physiological condition. In embodiments of the present invention that are described hereinbelow, photoplethysmograph signals that are captured while the patient sleeps are analyzed in order to diagnose the patient's cardiorespiratory condition. In particular, the signals may be used to detect and assess the severity of conditions that are characteristic of heart failure (HF), such as premature ventricular contractions and Cheyne-Stokes breathing. The photoplethysmograph signals may also be used, even without monitoring other physiological parameters, to classify the sleep stages and "sleep quality" of the patient.

The power and versatility of the photoplethysmograph-based techniques that are described hereinbelow make it possible to monitor patients' oxygen saturation, heartbeat, respiration, sleep stages and autonomic nervous system during sleep using no more than a single pulse oximeter probe (which typically clips onto the patient's finger). As a result, the patient may be monitored comfortably and conveniently, at home or in a hospital bed, even without on-site assistance in setting up each night's monitoring.

In alternative embodiments, the principles of the present invention may be applied to analysis of respiration signals captured using monitors of other types.

There is therefore provided, in accordance with an embodiment of the present invention, a method for diagnosis, including:

Receiving a signal associated with blood oxygen saturation of a patient during sleep;

filtering the signal so as to eliminate signal components at frequencies equal to and greater than a respiratory frequency of the patient; and processing the filtered signal to detect a pattern corresponding to multiple cycles of periodic breathing.

In disclosed embodiments, processing the filtered signal includes detecting the signal components that have a period greater than a minimum period of at least 30 sec, wherein the minimum period may be at least 55 sec.

In some embodiments, processing the filtered signal includes detecting occurrences of a pattern of Cheyne-Stokes breathing, and the method includes determining a prognosis of heart failure (HF) in the patient based on the occurrences of the pattern of Cheyne-Stokes breathing. Determining the prognosis may include predicting a probability of survival of the patient or predicting a level of at least one marker, selected from a group of markers consisting of Brain Natriuretic Peptide (BNP) and N-terminal prohormone Brain Natriuretic Peptide (NT proBNP). Additionally or alternatively, determining the prognosis may include differentiating compensated from decompensated heart failure, predicting a hospitalization of the patient, or providing an indication of a need for a change in treatment of the patient.

In one embodiment, receiving the signal includes receiving a photoplethysmograph signal from a sensor coupled to a body of a patient, and the method includes processing the photoplethysmograph signal so as to identify a cardiac arrhythmia of the patient. Typically, determining the prognosis includes finding the prognosis responsively both to the occurrences of the pattern of Cheyne-Stokes breathing and to the cardiac arrhythmia.

In some embodiments, determining the prognosis includes assessing a duration of the occurrences of a pattern of Cheyne-Stokes breathing. The method may include treating the patient so as to reduce the duration of the occurrences of the pattern of Cheyne-Stokes breathing. Additionally or alternatively, assessing the duration includes finding a cumulative duration of the occurrences of the pattern of Cheyne-Stokes breathing, and classifying the patient in a high-mortality group if the cumulative duration exceeds a predetermined threshold, typically at least 45 minutes.

Typically, detecting the occurrences includes identifying a Cheyne-Stokes breathing event when a duration of the multiple cycles is no less than a predetermined minimum duration. Additionally or alternatively, detecting the occurrences includes identifying a Cheyne-Stokes breathing event when a number of the multiple cycles is no less than a predetermined minimum number, such as three.

Further additionally or alternatively, detecting the occurrences includes identifying a Cheyne-Stokes breathing event when a representative level of the blood oxygen saturation during the cycles is less than the blood oxygen saturation before the cycles by at least a predetermined amount. The representative level of the blood oxygen saturation may be one of a median saturation, a mean saturation, and a minimum saturation during the cycles. Typically, the Cheyne-Stokes breathing event is identified when the representative level of the blood oxygen saturation is less than the blood oxygen saturation before the cycles by at least 2%.

In some embodiments, detecting the occurrences includes distinguishing the Cheyne-Stokes breathing events from obstructive apnea events. In one or these embodiments, distinguishing the Cheyne-Stokes breathing events includes determining a slope of the filtered signal, and distinguishing the Cheyne-Stokes breathing events responsively to the slope. Typically, determining the slope includes finding a measure of the slope selected from a group of measures consisting of a median slope and a mean slope, and distinguishing the Cheyne-Stokes breathing events based on a maximal value of the measure of the slope in each of the cycles. Distinguishing the Cheyne-Stokes breathing events may include classifying a breathing event as Cheyne-Stokes only when the maximal value of the measure is no greater than 0.7%/sec.

In another embodiment, the method includes screening the patient for heart failure based on the occurrences of the pattern of Cheyne-Stokes breathing.

In some embodiments, receiving the signal includes receiving a photoplethysmograph signal from a sensor coupled to a body of a patient, and the method includes processing the photoplethysmograph signal so as to measure a heart rate of the patient. Optionally, processing the photoplethysmograph signal includes identifying at least one premature ventricular contraction (PVC) in a heart rhythm of the patient. Additionally or alternatively, the method includes processing the photoplethysmograph signal so as to measure a vasomodulation in the body. Further additionally or alternatively, the method includes processing the photoplethysmograph signal so as to measure a modulation of respiration by the patient.

In one embodiment, receiving the signal includes receiving a photoplethysmograph signal from a sensor on a finger of the patient, and filtering the signal includes digitizing and filtering the signal so as to generate data using processing circuitry in a control unit that is fastened to a forearm of the patient, and storing the data in a memory in the control unit. Typically, processing the filtered signal includes connecting the control unit to an external processor and uploading the data from the memory to the external processor for analysis, and storing the data includes receiving and recording the data in the control unit while the control unit is disconnected from the external processor.

In another embodiment, receiving the signal includes receiving a photoplethysmograph signal from a sensor implanted in a body of the patient.

There is also provided, in accordance with an embodiment of the present invention, apparatus for diagnosis, including:

a sensor, which is configured to be coupled to a body of a patient during sleep and to output a signal associated with blood oxygen saturation in the body; and a processor, which is coupled to filter the signal so as to eliminate signal components at frequencies equal to and greater than a respiratory frequency of the patient, and to process the filtered signal to detect a pattern corresponding to multiple cycles of periodic breathing.

There is additionally provided, in accordance with an embodiment of the present invention, a computer software product, including a computer-readable medium in which program instructions are stored, which instructions, when read by a computer, cause the computer to receive a signal associated with blood oxygen saturation in a body or a patient, and to filter the signal so as to eliminate signal components at frequencies equal to and greater than a respiratory frequency of the patient, and to process the filtered signal to detect a pattern corresponding to multiple cycles of periodic breathing.

The present invention will be more fully understood from the following detailed description of the embodiments thereof, taken together with the drawings in which:

BRIEF DESCRIPTION OF THE DRAWINGS

FIG. 1 is a schematic, pictorial illustration of a system for sleep monitoring and diagnosis, in accordance with an embodiment of the present invention;

DETAILED DESCRIPTION OF EMBODIMENTS

System Overview

Figure 2A:
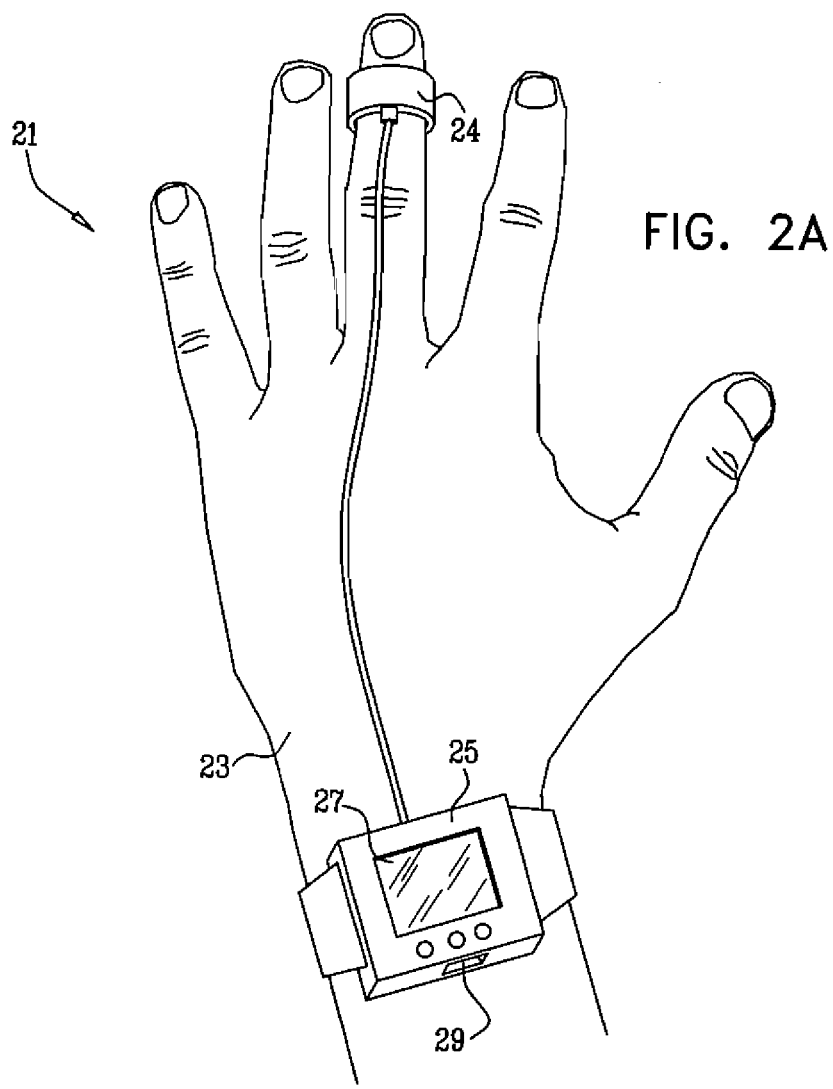
FIG. 2A is a schematic, pictorial illustration of apparatus for patient monitoring, in accordance with an embodiment of the present invention.

FIG. 1 is a schematic, pictorial illustration of a system 20 for sleep monitoring and diagnosis, in accordance with an embodiment of the present invention. In this embodiment, system 20 is used to monitor a patient 22 in a home, clinic or hospital ward environment, although the principles of the present invention may similarly be applied in dedicated sleep laboratories. System 20 receives and analyzes a photoplethysmograph signal from a suitable sensor, such as a pulse oximetry device 24. Device 24 provides a photoplethysmograph signal indicative of blood flow and a signal indicative of the level of oxygen saturation in the patient's blood. In the context of the present patent application and in the claims, the photoplethysmograph signal is thus considered to be a signal that is associated with blood oxygen saturation. Since the photoplethysmograph signal is modulated by both the heart rate and respiratory rate, it may also be used to provide a heart rate and respiratory rate signals. The sensor signals from device 24 are collected, digitized and processed by a console 28.

Optionally, system 20 may comprise sensors of other types (not shown), for collecting other physiological signals. For example, the system may receive an ECG signal, measured by skin electrodes, and a respiration signal measured by a respiration sensor. Additionally or alternatively, the techniques of monitoring and analysis that are described herein may be combined with EEG, EOG, leg motion sensors, and other sleep and/or cardiac monitoring modalities that are known in the art. As another example, console 28 may receive signals by telemetry from implantable cardiac devices, such as pacemakers and ICDs.

Console 28 may process and analyze the signals from pulse oximetry device 24 locally, using the methods described hereinbelow. In the present embodiment, however, console 28 is coupled to communicate over a network 30, such as a telephone network or the Internet, with a diagnostic processor 32. This configuration permits sleep studies to be performed simultaneously in multiple different locations. Processor 32 typically comprises a general-purpose computer processor (which may be embedded in a bedside or remote monitor) with suitable software for carrying out the functions described herein. This software may be downloaded to processor 32 in electronic form, or it may alternatively be provided on tangible media, such as optical, magnetic or non-volatile electronic memory. Processor 32 analyzes the signals conveyed by console 28 in order to analyze the physiological parameters, identify sleep stages, and extract prognostic information regarding patient 22, and to display the results of the analysis to an operator 34, such as a physician.

Alternatively, although the embodiments described herein relate mainly to methods and apparatus for monitoring and diagnosis during sleep, the principles of the present invention may also be applied, mutatis mutandis, to patients who are awake. In particular, these methods and apparatus may be used in monitoring patients who are reclining or otherwise at rest, even if they are not asleep.

Figure 2B:
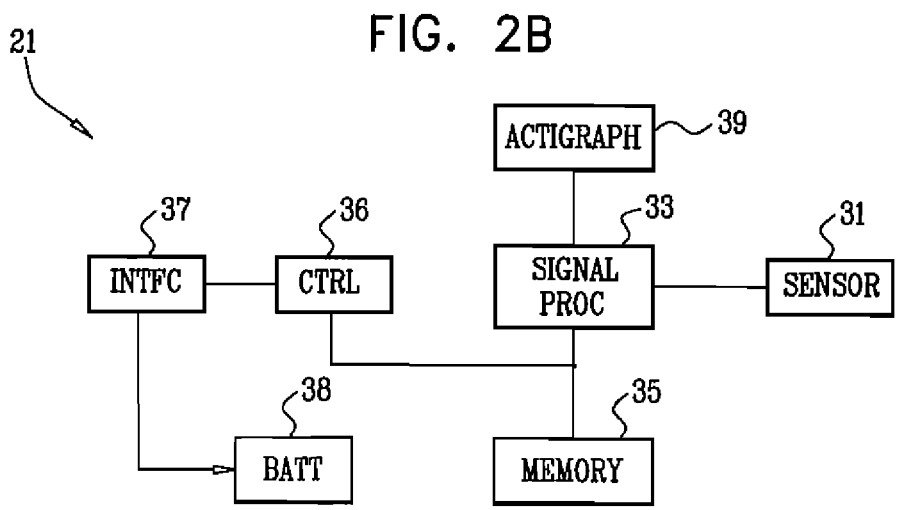
FIG. 2B is a block diagram that schematically shows functional elements of the apparatus of FIG. 2A, in accordance with an embodiment of the present invention.

Reference is now made to FIGS. 2A and 2B, which schematically illustrate apparatus 21 for patient monitoring, in accordance with an embodiment of the present invention. FIG. 2A is a pictorial illustration of the apparatus, while FIG. 2B is a block diagram showing functional components of the apparatus. Apparatus 21 is similar in functionality to elements of system 20, as shown in FIG. 1, but apparatus 21 is particularly advantageous in that it can be worn comfortably by the patient during both sleep and waking hours and requires no wired connection to a console, except periodically (once a day, for example) for data upload and battery recharging.

As shown in FIG. 2A, pulse oximetry device 24 in apparatus 21 has the form of a ring, which fits comfortably over one of the fingers on a hand 23 of the patient (although other configurations of device 24 may alternatively be used in the apparatus). Device 24 is connected by a wire to a control unit 25, which may conveniently be fastened around the patient's wrist. Alternatively, the control unit may be fastened elsewhere on the patient's forearm, at any suitable location between the hand and the elbow, or elsewhere on the patient's body. The control unit may include a display 27, to present status information and/or readings of monitored parameters, such as heart rate, blood oxygen saturation and heart failure status. A connector 29 on the control unit is configured to connect to a console or docking station. In the illustrated embodiment, connector 29 comprises a receptacle for a cable with a standard plug, such as a USB cable. Alternatively, the connector may mate directly with a matching connector on a dedicated docking station.

Figure 3A:
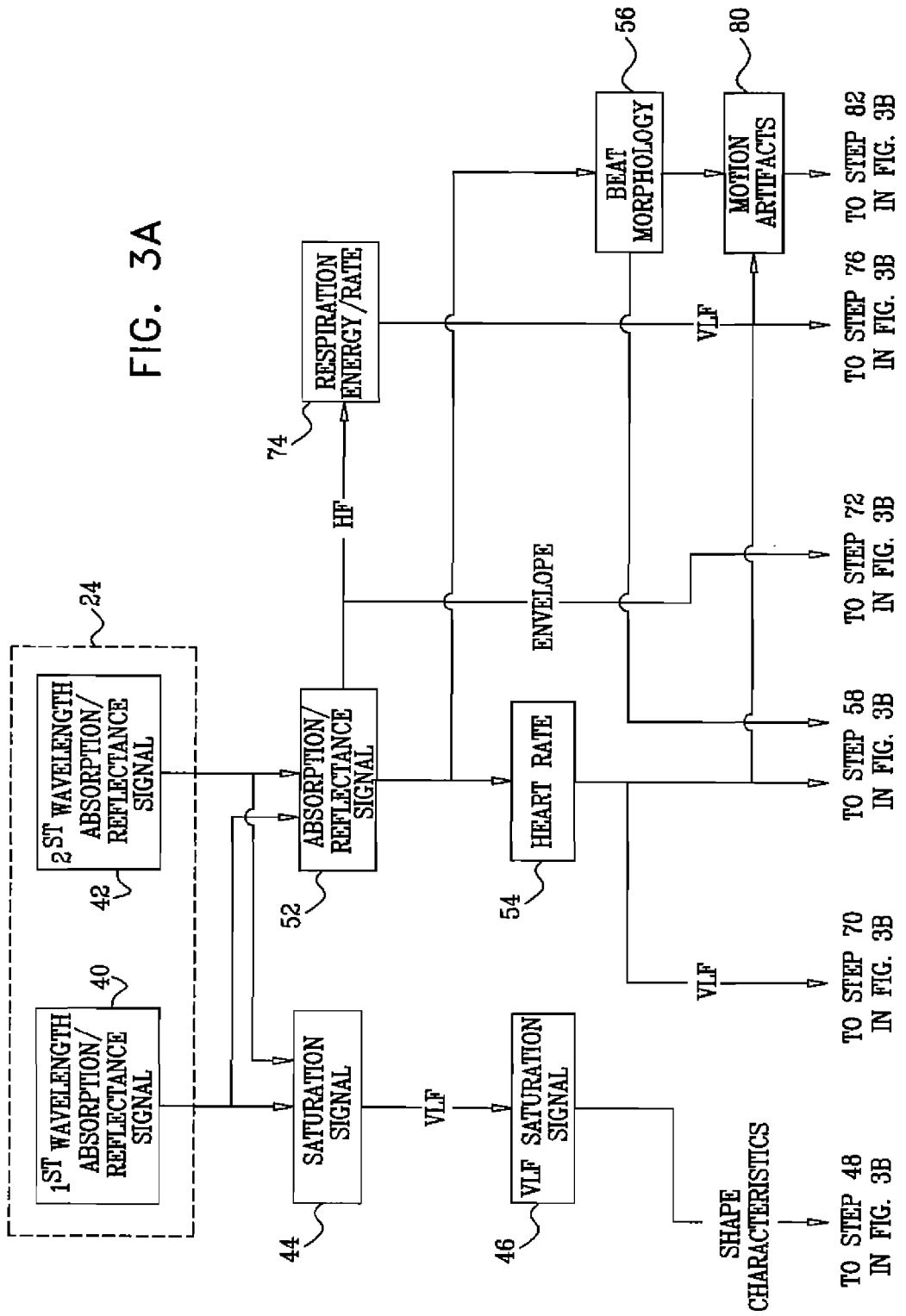
FIGS. 3A and 3B are a flow chart that schematically illustrates a method for sleep monitoring and diagnosis, in accordance with an embodiment of the present invention.
Figure 3B:
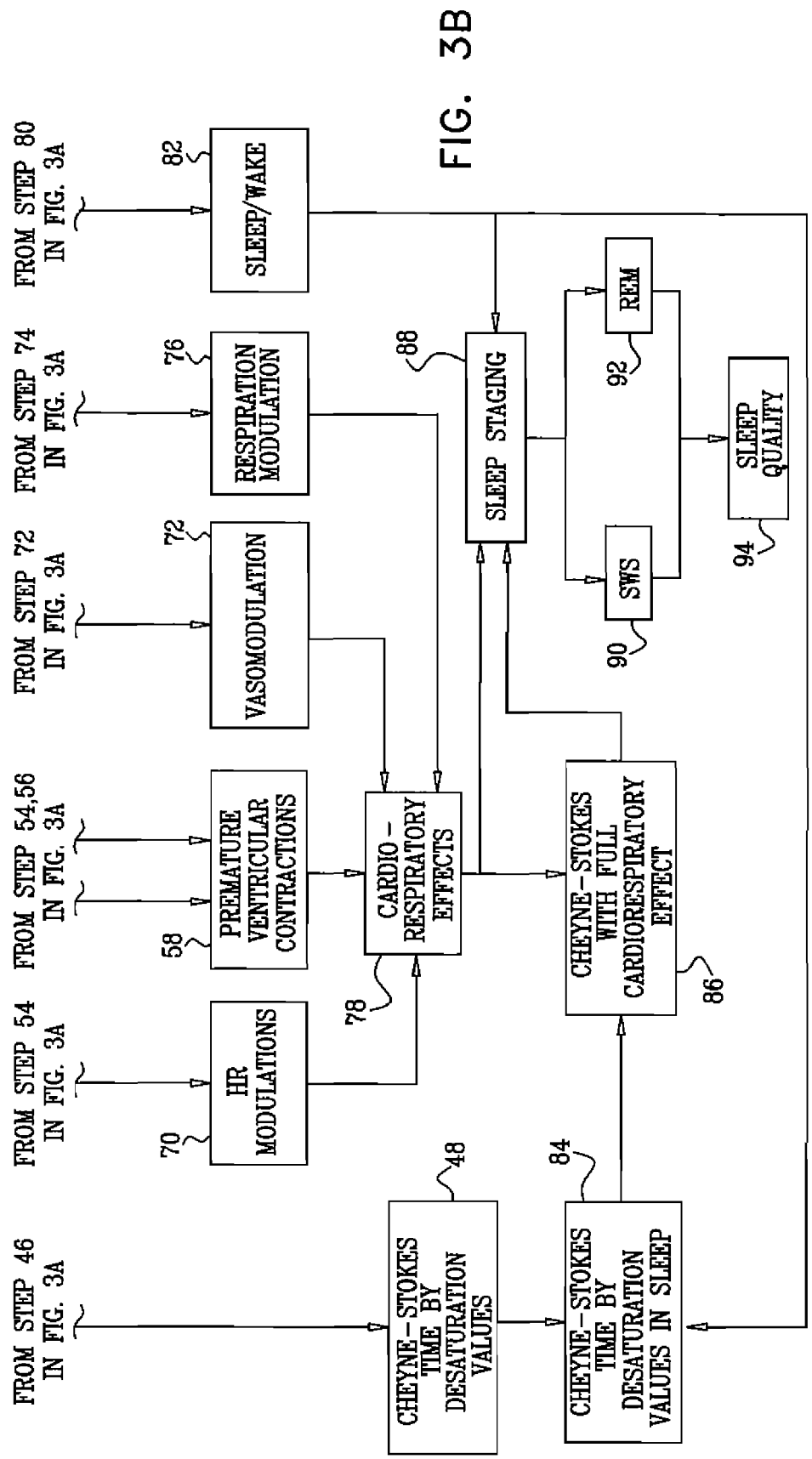

As shown in FIG. 2B, a sensor 31 (typically comprising two light source/light detector subassemblies, as described below) in device 24 is connected via wire to signal processing circuitry 33 in control unit 25. The signal processing circuitry digitizes and filters the signals from sensor 31 and stores the results in a memory 35. (Alternatively or additionally, control unit 25 may transmit the results to a receiver using a suitable wireless communication protocol, such as Bluetooth® or ZigBee®). Optionally, circuitry 33 may also be configured to perform some of the additional processing functions that are shown in FIGS. 3A and 3B and described hereinbelow. The signal processing circuitry and peripheral components are powered by an internal power source, such as a battery 38, so that apparatus 21 can perform its data collection functions without wired connection to a console or to lines power.

Apparatus 21 may also comprise an actigraph 39, which is typically contained in control unit 25. The actigraph measures movement of the patient and typically comprises an accelerometer for this purpose. The measurements of patient movement are recorded together with the data from sensor 31 in memory 35 and may be used in subsequent analysis to determine the patient's state of sleep or arousal.

After apparatus 21 has recorded patient data in memory 35 for a sufficient period of time, the user (who may be the patient himself or herself) connects control unit 25 to the docking station or other console via connector 29. A controller 36 in the control unit is then able to communicate with the console or docking station via a suitable interface 37 (such as a USB interface in the example noted above). The controller reads out the data that are stored in memory 35 to a processor, such as processor 32, which analyzes the data, as described hereinbelow. In addition, interface 37 may comprise charging circuitry for recharging battery 38.

In the embodiments that are described below, pulse oximetry device 24 may be configured either as shown in FIG. 1 or as shown in FIG. 2A or 2B. Alternatively, substantially any suitable sort of photoplethysmograph may be used in these embodiments, including a photoplethysmographic sensor that is implanted in the body of the patient. An implantable oximeter that may be used for this purpose, for example, is described in U.S. Pat. No. 6,122,536, whose disclosure is incorporated herein by reference. Furthermore, the methods that are described hereinbelow may be used in conjunction with devices of other types that provide information on the breathing, oxygen saturation, and heart performances of the patient. In one embodiment, for instance, the methods described below are applied to the output of a non-contact respiratory monitor, such as the one described in U.S. Pat. No. 6,011,477, whose disclosure is incorporated herein by reference.

Diagnostic Method

FIGS. 3A and 3B are a flow chart that schematically illustrates a method for sleep monitoring and diagnosis, in accordance with an embodiment of the present invention. Pulse oximetry device 24 comprises two light source/light detector subassemblies 40 and 42. These subassemblies generate signals that are indicative of absorption and/or reflectance of light at two different wavelengths, typically one red and one infrared, as is known in the art. Each signal includes an AC component, which corresponds to the pulsatile change in the signal at the patient's heart rate, and a slow-changing DC component. Comparison of the AC components of the two signals gives a blood oxygen saturation signal 44. Alternatively, at least some of the methods described below can use the signals from only a single source/detector subassembly, or signals provided by other types of photoplethysmographic sensors.

The saturation signal is low-pass filtered to give a very-low-frequency (VLF) saturation signal 46. This filtering removes signal components at frequencies that are greater than or equal to the patient's respiratory frequency, so that the signal remaining reflects trends over multiple respiratory cycles. In some embodiments, the filtering is even more pronounced, and eliminates frequency components outside the Cheyne-Stokes cycle frequency, for example, components below $1/180$ Hz or above $1/40$ Hz.

Processor 32 analyzes shape characteristics of the VLF saturation signal in order to detect episodes of Cheyne-Stokes breathing (CSB). As noted earlier, this condition is characterized by a regular waxing and waning breathing pattern and occurs particularly among patients with heart failure and in patients who have experienced a stroke. CSB is present during sleep, and in more severe cases may also be observed during wakefulness. According to the American Academy of Sleep Medicine, Cheyne-Strokes breathing syndrome (CSBS) is characterized by the following criteria:

1. Presence of congestive heart failure or cerebral neurological disease.
2. Respiratory monitoring demonstrates:
   a. At least three consecutive cycles of a cyclical crescendo and decrescendo change in breathing amplitude. Cycle length is most commonly in the range of 60 seconds, although the length may vary.
   b. One or both of the following:
      i. Five or more central sleep apneas or hypopneas per hour of sleep.
      ii. The cyclic crescendo and decrescendo change in breathing amplitude has duration of at least 10 consecutive minutes.

The inventors have found the typical Cheyne-Stokes cycle length to be between 40 and 90 sec. The decrescendo phase is associated with decreased respiratory effort and rate (hypopnea/apnea); decrease in oxygen saturation; decrease in heart rate; and vasodilation, manifested in decreased blood pressure. The crescendo phase has the opposite effects: increase in respiratory effort and rate, i.e. hyperpnea; increase in heart rate; and vasoconstriction, leading to increased blood pressure. Sometimes the hyperpnea is accompanied by an arousal, which is manifested as a motion artifact in the photoplethysmograph signal. The changes in heart rate and vasomotion (dilation and constriction) depend on the severity of the heart failure, as discussed below.

The inventors have also found that decompensated heart failure patients nearly always present long sequences of periodic Cheyne-Stokes breathing episodes, with a cycle length between 55 and 180 seconds. In general, the longer the cycle length, the more severe is the state of the disease. Therefore, processor 32 uses the shape characteristics of the VLF saturation signal in measuring time characteristics 48 of the patient's Cheyne-Stokes episodes. Specifically, the processor detects desaturation episodes extending over multiple consecutive Cheyne-Stokes breathing cycles in order to identify the presence of CSBS.

In order to detect and measure the duration of multi-cycle Cheyne-Stokes episodes, processor 32 typically locates the local maxima and local minima of the VLF saturation signal. The processor may also compute the difference between the maximal and minimal saturation values (in the unsmoothed saturation signal 44), as well as the corresponding wavelengths. The processor extracts time sequences of cyclic breathing with similar desaturation values and similar wavelengths, falling in the range that is characteristic of Cheyne-Stokes cycles. (Typically only a certain percentage, such as 80%, of the desaturation and wavelength values are required to be close to the median values of the sequence, in order to avoid losing sequences due to intervening outliers. For example, a 50% deviation from the median value of 80% of the wavelength and desaturation values may be accepted for a sequence that is at least of a certain minimum duration, such as 5 min.) The processor chooses the longest segments that meet the above similarity criteria. Alternatively, a hysteresis procedure may be used to ensure robustness against outliers. The total Cheyne-Stokes time is then computed as the total duration of all the segments that are classified as Cheyne-Stokes breathing events.

In order to validate the automatic measurements of Cheyne-Stokes episodes described above, the inventors conducted a clinical trial, which included 91 full-night ambulatory polysomnography tests for patients with advanced heart failure. Cheyne-Stokes episodes were marked manually by an experienced scorer, and these manual results were compared to the results of the automatic process described above. The correlation between manual automatic scoring was 83%, which is as good as the typical correlation between different human scorers.

To ensure further that the sequences of cyclic breathing episodes are indeed associated with the severity of heart failure status, processor 32 evaluates the slope of the saturation signal (or of the DC component of the pulse oximeter signal) for each desaturation event. In central apnea, or when the heart failure state is grave, the slope of the exit from the cycle is moderate, i.e., it is similar to the typical (or specific) entry slope. Therefore, to identify a time sequence of cyclic breathing as Cheyne-Stokes, processor 32 requires that the sequence comprise mainly (typically at least 80%) events of moderate slope. (The above-mentioned PCT Patent Application PCT/IL2006/000148 defines formal criteria for assessing the symmetry of periodic breathing episodes, which may also be used in the present context for distinguishing Cheyne-Stokes events.) This requirement of moderate slope may be applied to the median slope value.

These observations with respect to the symmetry of the periodic breathing patterns apply both to the slowly-varying heart rate and saturation signals and to the envelopes of the other, rapidly-varying signals shown by the other traces. The term "envelope" in this context typically means a signal derived from the local minima and/or local maxima of another signal, with or without smoothing (by convolution or resampling, for example) "Envelopes" may also be derived by other mathematical operations known in the art, such as application of Hilbert transforms. The inventors have found that periodic breathing patterns associated with CSA generally tend to be more symmetrical than the patterns associated with OSA, presumably due to the different physiological mechanisms that are involved in the different types of apneas. Therefore, processor 32 may validate the prognostic value of the Cheyne-Stokes marker by considering only events with mild exit slope from desaturation events. The inventors found that computing the slope of the saturation curve by fitting a line (by the least-square method) to the curve over a nine-second epoch, and requiring that the slope of the line be less then 0.7 percent/second is a good implementation of this mild desaturation condition.

Processor 32 associates each segment with its segment duration and with its median desaturation value. The features of the Cheyne-Stokes segments are prognostic of patient outcome in cases of heart failure (and other illnesses). Long wavelength, in particular, is associated with bad prognosis. Thus, processor 32 typically detects signal components that have a period greater than a minimum period of at least 30 sec. In the marker validation experiments that are described herein, the inventors required the median cycle length to be above 55 seconds and the median desaturation value to be no less the 2% in order to classify a periodic breathing pattern as Cheyne-Stokes breathing.

On the other hand, time segments with steep exit saturation slope typically correspond to obstructive apnea/hypopnea events. Other features of obstructive apnea/hypopnea time segments include short wavelength, large vasomotion, and large heart rate modulations. These phenomena are generally associated with good prognosis, since they reflect the patient's ability to manifest enhanced sympathetic activity.

In addition to the saturation measurements and Cheyne-Stokes detection, processor 32 may also process an AC absorption or reflectance signal 52 that is output by device 24 in order to compute a heart rate 54, as is known in the art. Furthermore, the AC signal may be analyzed to detect a beat morphology 56. The processor identifies certain aberrations in this morphology as arrhythmias, such as premature ventricular contractions (PVCs) 58. It keeps a record of the occurrences of such arrhythmias, in a manner similar to a Holter monitor, but without requiring the use of ECG leads. The total number of abnormal heart beats and (specifically PVCs) that are accumulated in such a record, particularly during sleep, is indicative of bad prognosis. As the inventors have found that premature beats during sleep have the greatest prognostic value for advanced heart failure patients, the processor may be configured to count the number of premature beats only during sleep or during episodes of Cheyne-Stokes breathing.

Figure 4:
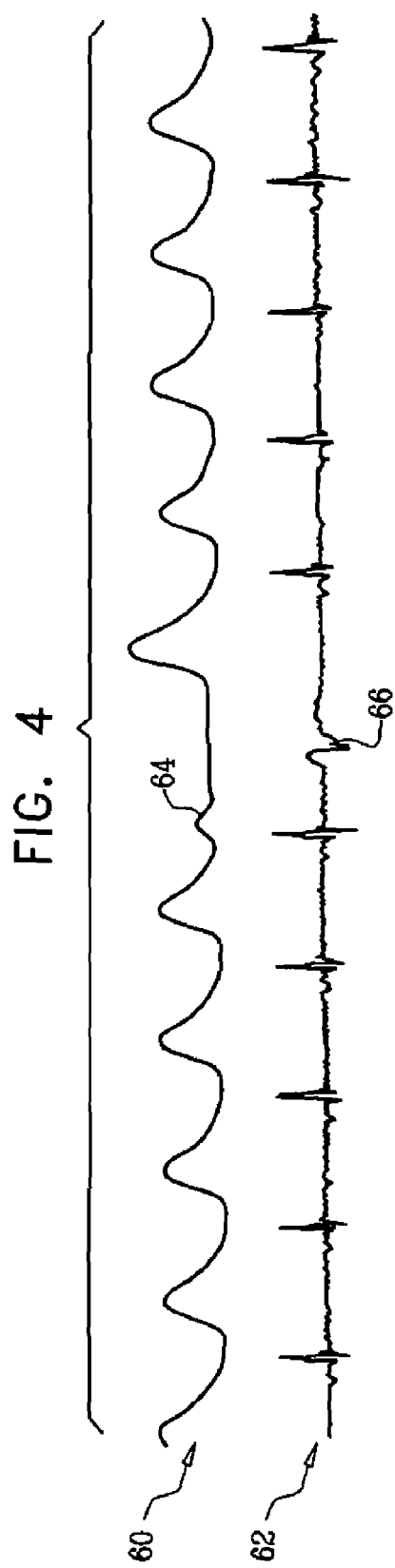
FIG. 4 is a schematic plot of photoplethysmograph and ECG signals, illustrating detection of a cardiac arrhythmia in accordance with an embodiment of the present invention.

FIG. 4 is a schematic plot of an AC photoplethysmograph signal 60, alongside a corresponding ECG signal 62, illustrating a method for detection of PVCs in accordance with an embodiment of the present invention. Signal 60 can be seen to comprise a series of regular waveforms, which are indicative of arterial blood flow. A PVC is manifested as an aberrant waveform 64 in signal 60, and likewise by an abnormal waveform 66 in signal 62. Processor 32 analyzes the shape, amplitude and timing of waveform 64 in the plethysmograph signal in order to determine that the aberrant wave represents PVC, even without the use of any sort of ECG monitoring.

In one embodiment, arrhythmias are identified in photoplethysmograph signal 60 based on the following features:
1. Local maxima and minima are extracted from the signal in segments of the signal whose length is less than the typical RR interval (i.e., the typical time difference between successive heart beats). For example, 0.3 seconds is an appropriate segment length for this purpose.
2. The width of each beat is defined, for example by measuring the time difference between successive locations of photoplethysmograph signal values whose energy is equal to the average (possibly a weighted average) of the local maximum and minimum.
3. Beats with short width typically correspond to PVCs, as shown in FIG. 4. The number of such beats is a measure of the severity of arrhythmia.
4. An additional criterion for detecting an arrhythmia is that the time span of two beats, one of which has a short width, is roughly equal to the time span of two normal beats.

Although FIG. 4 and the above description relate specifically to PVCs, the principles of this embodiment may likewise be applied in detecting other types of premature heart beats, as well as various other types of heartbeat irregularities. Such irregularities are associated with reduced stroke volume, which in turn affect the amplitude, width and other features of the photoplethysmograph waveform.

Other types of aberrant waveforms in photoplethysmograph signal 60 may correspond to motion artifacts 80 (listed in FIG. 3A, but not shown in FIG. 4). Motion is characterized by local maxima well above normal beat range (for example, at least twice the normal value). The prevalence of motion artifacts can be used in detecting movement, which indicate whether the patient is in a sleep or waking state 82. Alternatively or additionally, a motion sensor may be used to detect arousals.

Referring further to FIGS. 3A and 3B, processor 32 may additionally extract other cardiorespiratory parameters from signal 52, either directly or indirectly. For example, the processor may apply very-low-frequency filtering to heart rate 54 in order to detect heart rate modulations 70. Additionally or alternatively, the envelope of signal 52 may be processed in order to detect characteristics of vasomodulation 72, i.e., arterial dilation and constriction.

Further additionally or alternatively, processor 32 may compute a respiration energy and/or rate characteristic 74 based on high-frequency components of signal 52. Respiratory sinus arrhythmia is a natural cycle of arrhythmia that occurs in healthy people through the influence of breathing on the flow of sympathetic and vagus impulses to the sinoatrial node in the heart. This effect may be used to calculate respiration from heart rate. Well-treated heart failure patients, however, are frequently under the control of cardiac pacemakers and often take beta-blockers and ACE inhibitors that suppress this phenomenon. High-frequency (10-30 cycles/min, i.e., 0.17-0.5 Hz) filtering of the photoplethysmograph signal enables the processor to determine respiration energy and/or rate characteristics in these cases, as well.

Very-low-frequency components of characteristic 74 are indicative of a respiration modulation 76. Processor 32 combines the various cardiac, respiratory and vasomodulation parameters described above in order to provide a general picture of cardiorespiratory effects 78, all on the basis of the photoplethysmograph signals.

Similar procedures to those described above can be applied to the detrended AC photoplethysmograph signal. One way to perform detrending is to replace the photoplethysmograph signal with its amplitude feature (maximum minus minimum signal). Other methods include subtracting a polynomial that approximates the signal, or using local maxima or local minima features. Following detrending, the processor applies very-low-frequency filtering followed by outlier rejection, and then computes the median vasomotion of each sequence.

The processor may perform similar analyses on heart rate and respiratory signals from other sources. Arousals can estimated from motion artifacts as described above or from other data if available (such as EEG alpha and beta frequencies, or scorer marking, or a motion sensor).

Information regarding sleep/wake state 82 is combined with Cheyne-Stokes time 48 to determine specific, cumulative Cheyne-Stokes time 84 during sleep. The total Cheyne-Stokes time and percentage of Cheyne-Stokes time during sleep have prognostic value: A large percentage of Cheyne-Stokes time is associated with mortality and high levels of brain natriuretic peptide (BNP), which are associated with severity of heart failure. Furthermore, information about sleep time can be used to ensure that low Cheyne-Stokes duration is not associated with little or no sleep. (The inventors have determined the prognostic value of total Cheyne-Stokes time only in patients who slept for at least a certain minimal duration, such as two hours.) The prognostic value of Cheyne-Stokes information derived in the above manner is illustrated in FIGS. 5-8 below.

This information regarding Cheyne-Stokes time 84 in turn is combined with the general picture of cardiorespiratory effects 78 in order to provide some or all of the following combined information 86 for each Cheyne-Stokes sequence during sleep:
1. duration
2. median wavelength
3. median desaturation
4. median vasomotion
5. median heart rate modulation
6. median respiratory modulation
7. number of PVCs and other premature beats.
8. arousal index: number of arousals Alternatively, the above-mentioned median functions may be replaced by similar functions based on average values or average of values in the middle tertile, inter-quartile range, or any other appropriate segment. Each of the above parameters can also be computed separately for REM sleep and NREM sleep.

In an exemplary embodiment, the following criteria may be applied to the various processed outputs of oximetry device 24 in order to derive information 86 and measure the manifestations of Cheyne-Stokes breathing:
1. The saturation signal is filtered in the Cheyne-Stokes frequency range, typically $\frac{1}{180}$-$\frac{1}{40}$ Hz.
2. A time segment is identified as a Cheyne-Stokes event (and the durations of such time segments are summed) if the segment contains a sequence of at least three cycles of desaturation for which:
   a. Median desaturation (compared to the previous saturation level) is at least 2%. Alternatively, another representative saturation level, such as the mean or minimum, may be used.
   b. Mean cycle length is long (55-180 sec). (Short cycle length is not associated with bad prognosis.)
   c. Cycle length fluctuation within each sequence may optionally be limited (to less then 10% fluctuation, for example).
   d. Moderate vasomotion, based on at least one of the following:
      i. Median of maximal desaturation slope in each cycle is less then a maximum slope limit, such as 0.7 percent/sec. (by least squares fit of a line to the desaturation curve). Alternatively, a measure of mean slope may be used.
      ii. Only moderate fluctuations (typically no greater than 10% of the normal range) occur in the VLF range of the detrended respiration signal.
3. Optionally, for a periodic breathing cycle to be identified as part of a Cheyne-Stokes event, respiration characteristic 74 may be required to reach a minimum indicating zero respiratory effort during the cycle. This minimum may be identified based on the VLF components of characteristic 74 in respiration modulation 76.
4. Outlier rejection procedures may be applied to the saturation and respiration values before classifying time segments. For example:
   a. As noted above, a certain fraction (typically up to 20%) of the desaturation and wavelength values may be far from the median values of the sequence, and extreme desaturations (for example, >50%) may be rejected as faulty readings.
   b. The mean cycle length can be calculated after discarding values that are far from the mean (for example, values in the top and bottom deciles.)
   c. Consistency may be enforced by permitting the relation between cycle length and desaturation to vary linearly within given bounds.
5. In addition to or instead of the above criteria, self-similarity measures can be used in identifying sequences of Cheyne-Stokes cycles. For example, a distinct peak in the $\frac{1}{180}$-$\frac{1}{40}$ Hz range of the Fourier transform of the sequence of periodic breathing cycles or high autocorrelation of the cycles is an indicator of such self-similarity.

Similarly, when a respiration signal is obtained without a saturation signal, Cheyne-Stokes respiration segments can be found by applying the above criteria to the respiration signal (excluding the computations that relate to saturation values).

Referring again to FIG. 3B, sleep/wake state 82 may be combined with analysis of cardiorespiratory and Cheyne-Stokes effects in order to perform automatic sleep staging 88. All of the factors that are used in determining the sleep stage may be derived solely from the signals generated by oximetry device 24. Alternatively, other signals may be incorporated into the sleep staging calculation.

Sleep states are classified by processor 32 as light sleep, deep slow-wave sleep (SWS) 90 and REM 92. During REM sleep, the patient is partially paralyzed, so that there is no motion. Furthermore, due to the changes in autonomic control and the partial paralysis that characterize REM sleep, the Cheyne-Stokes wavelength tends to be longer and the desaturation deeper in REM sleep that in light sleep. On the other hand, there are no apnea episodes in deep sleep. Others factors characterizing deep sleep include regularity of respiratory cycle length and low vasomotion.

Processor 32 may use the distribution of sleep stages and of apnea events during sleep in computing a sleep quality index 94. Typically, high percentages of REM and SWS, as well as apnea-free (or nearly apnea-free) segments in non-SWS sleep, are indicative of good prognosis for heart failure patients. By contrast, low percentages of REM or SWS indicate a poor prognosis. Further aspects of sleep staging and sleep quality assessment are described in the above-mentioned PCT patent applications.

CLINICAL APPLICATION AND RESULTS

The methods described above for measuring and quantifying Cheyne-Stokes breathing and attendant heart failure prognosis may be used conveniently in performing frequent checks on patient status, both at home and in the hospital. Additionally or alternatively, occasional checks of this sort may be used for risk stratification and screening. As explained above, these methods may be implemented using measurements made solely by pulse oximetry device 24, or alternatively in conjunction with other sensors, as in a multi-monitor polysomnography system, or in an implantable device, or using other types of respiratory sensors.

The inventors compared Cheyne-Stokes time with heart failure status in 91 tests of advanced heart failure patients. Results of this study are presented below. The cumulative duration of Cheyne-Stokes breathing during a night's sleep was measured, wherein Cheyne-Stokes cycles were identified as described above (including the requirements of mild slope—up to 0.7 percent/sec, median desaturation of at least 2%, and median cycle length of 55 to 180 sec.) The status of the patients was determined by six-month survival and BNP levels, which are generally considered the best marker for heart failure status. For this purpose, a blood sample was drawn from each patient and tested for NT-proBNP on the night of the sleep study. Serum N-terminal prohormone Brain Natriuretic Peptide (NT-proBNP) was measured using the Elecsys® proBNP electro-chemiluminescence immunoassay, run on the Elecsys 1010 benchtop analyzer (Roche Diagnostics, Indianapolis, Ind.).

Figure 5:
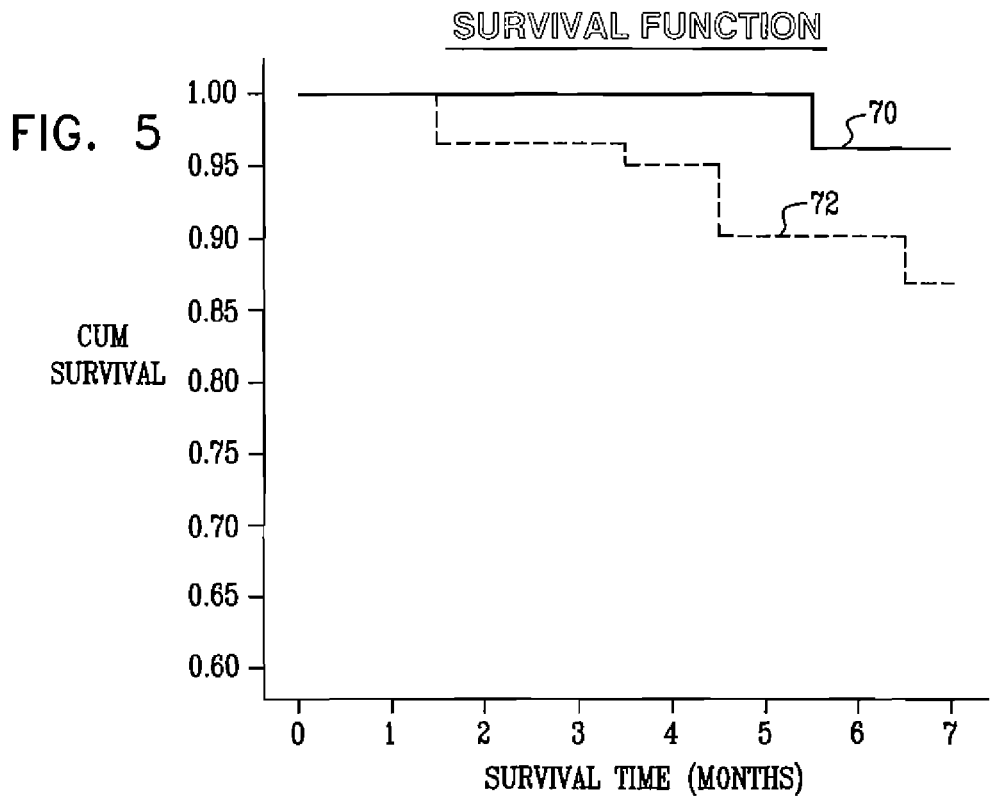
FIG. 5 is a Kaplan-Meier plot that schematically shows survival of heart failure patients as a function of Brain Natriuretic Peptide (BNP) levels.

FIG. 5 is a Kaplan-Meier plot of patient survival according to the standard BNP kit values. According to accepted diagnostic standards, a state of decompensated heart failure is associated with a serum NT-proBNP level above 450, 900, or 1,800 pg/mL for patients whose age is less than 50, 50-75, or above 75, respectively. An upper trace 70 shows the rate of survival over time for the patients with low BNP (below the decompensation threshold), while an upper trace 72 shows the rate for patients with high BNP. The odd ratio for dying among patients with high (decompensated) BNP values was 3.5 times higher then for patients in the low-BNP group. This result, however, was not statistically significant in this trial ($p=0.18$).

Figure 6:
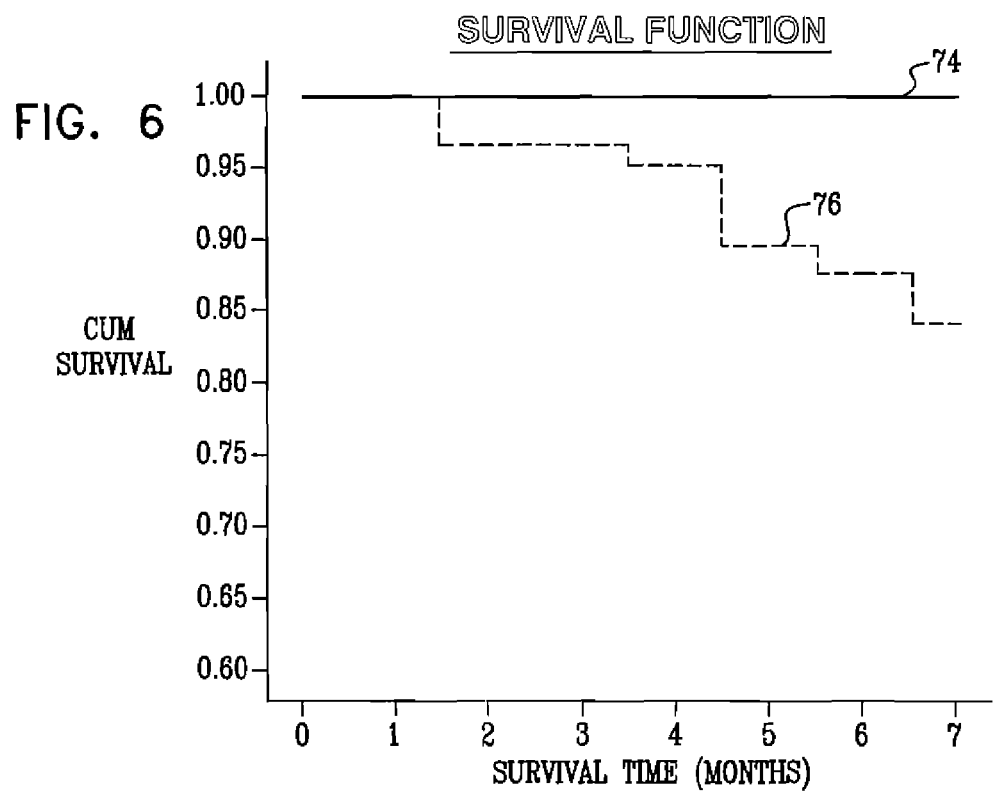
FIG. 6 is a Kaplan-Meier plot that schematically shows survival of heart failure patients as a function of BNP levels, with a threshold level determined by severity of Cheyne-Stokes breathing, in accordance with an embodiment of the present invention.

FIG. 6 is a Kaplan-Meier plot of patient survival according to the automated Cheyne-Stokes marker described above, in accordance with an embodiment of the present invention. In this figure, an upper trace 74 shows the survival rate of the patients who had low cumulative duration of Cheyne-Stokes breathing episodes, while a lower trace 76 shows the survival rate for patients with high cumulative Cheyne-Stokes duration. The inventors have found that typically, a cumulative duration of Cheyne-Stokes breathing episodes in excess of 45 minutes during a night's sleep is indicative of poor prognosis. In the results shown in FIG. 6, the Cheyne-Stokes cutoff (48 minutes) was selected to best predict BNP cutoff according to the standard guidelines described above.

Comparison of FIGS. 5 and 6 shows that the respiration-based measure of heart failure severity is superior to the standard BNP test in predicting mortality: The odd ratio for dying among patients with high Cheyne-Stokes duration is better then 5.2. (There was no mortality at all in the low Cheyne-Stokes group.) The results are statistically highly significant (p=0.017). For some higher cutoff points of Cheyne-Stokes time, the odd ratio improved even further. Furthermore, these results also demonstrate that Cheyne-Stokes duration is a strong predictor of BNP level and differentiates between compensated and decompensated levels of heart failure.

Figure 7:
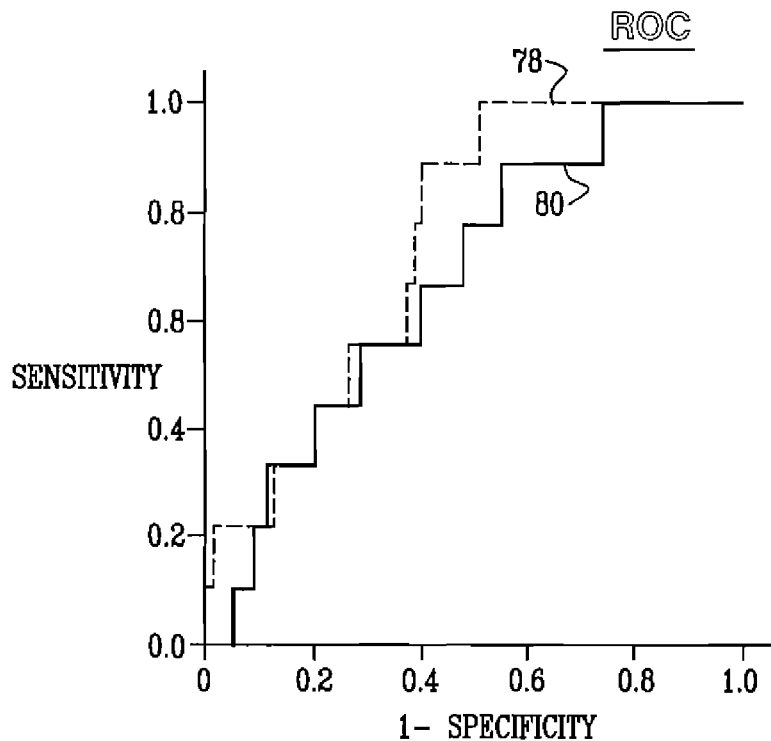
FIG. 7 is a receiver operating characteristic (ROC) plot, which schematically shows the sensitivity and specificity of predicting heart failure prognosis in accordance with an embodiment of the present invention.

FIG. 7 is a receiver operating characteristic (ROC) plot, which schematically compares the sensitivity and specificity of predicting heart failure prognosis using BNP and duration of Cheyne-Stokes breathing episodes, as measured in accordance with an embodiment of the present invention. An upper trace 78 is the ROC curve for Cheyne-Stokes duration, while a lower trace 80 is the ROC curve for the BNP marker. To derive the results shown in the figure, both Cheyne-Stokes duration and BNP were tested against six-month mortality of the patients in the study. The plot shows that the Cheyne-Stokes marker gives greater sensitivity and specificity. The area under the curve (AUC) for BNP is 68% (p=0.082), while it is 75% (p=0.015) for the Cheyne-Stokes marker.

Figure 8:
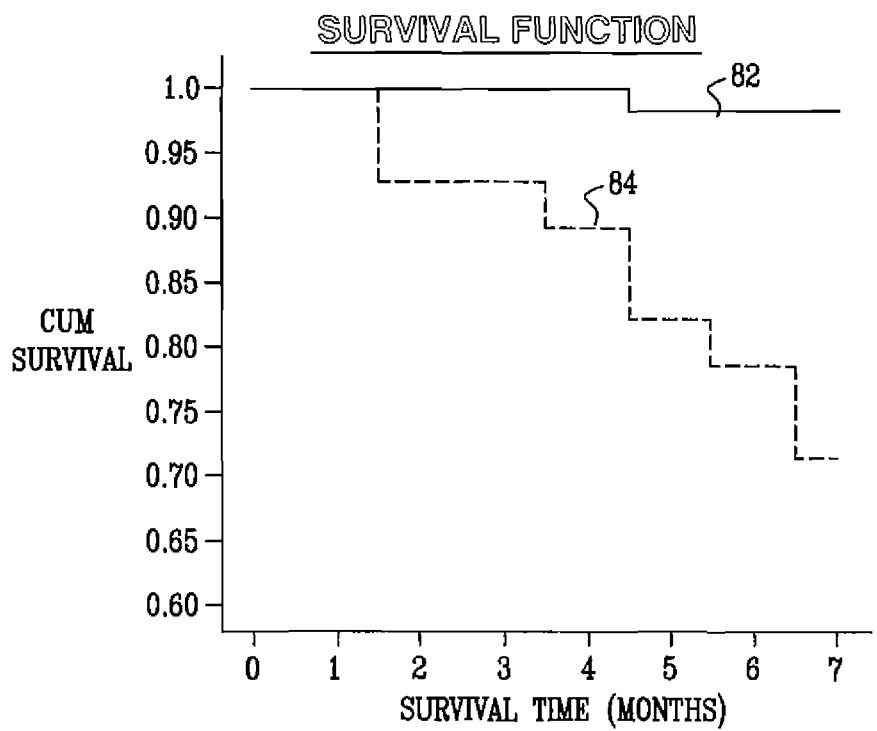
FIG. 8 is a Kaplan-Meier plot that schematically shows survival of heart failure patients as a function of the severity of symptoms classified by a method in accordance with an embodiment of the present invention.

FIG. 8 is a Kaplan-Meier plot of six-month survival of the heart failure patients as a function of the severity of symptoms classified by the methods described above, in accordance with another embodiment of the present invention. In this case, patients were classified into two groups: one group with severe Cheyne-Stokes breathing coupled with cardiac arrhythmia, and the other with breathing and heart rhythm that showed mild or no symptoms of these kinds. For this purpose, patients who exhibited at least 200 premature beats in the course of the night's sleep were classified as suffering from cardiac arrhythmia. An upper trace 82 in the figure shows the survival rate for the group with mild or no symptoms, while a lower trace 84 shows the survival rate for patients in the severe/arrhythmic group. The plot demonstrates that the combined detection of Cheyne-Stokes breathing and cardiac arrhythmias is an even stronger predictor of survival than Cheyne-Stokes breathing by itself: The odd ratio in this case was 17.7 with p=0.000.

The results of FIGS. 5-8 show that photoplethysmographic monitoring during sleep may be used effectively for the prognosis of heart failure patients. As explained above, this sort of monitoring is simple to carry out in the patient's home or hospital bed and may be performed at regular intervals, at low cost and minimal discomfort to the patient. It provides physicians with an accurate prognostic indicator, which they can use in choosing the optimal treatment, such as determining whether a patient requires hospitalization, and adjusting treatment parameters (such as drug titration) based on changes in the patient's condition. For example, using the techniques described above, the physician may measure and quantify the patient's symptoms (Cheyne-Stokes duration and possibly arrhythmias) prior to initiating or making a change in treatment, and may repeat the measurement thereafter in order to assess the effectiveness of the treatment and possibly readjust treatment parameters.

As another alternative, the physician may fix a specific critical Cheyne-Stokes duration for individual patients, and then set a monitoring system to alarm whenever a specific duration is exceeded.

Although the embodiments described above relate mainly to signals captured by pulse oximetry device 24, the principles of the present invention may be applied to respiration signals captured by any other suitable type of sensor. Such sensors may be based, for example, on electrical measurements of thoracic and abdominal movement, using skin electrodes to make a plethysmographic measurement of the patient's respiratory effort, or a belt to sense changes in the body perimeter. Additionally or alternatively, air flow measurement, based on a pressure cannula, thermistor, or $CO_2$ sensor, may be used for respiration sensing. In other embodiments of the present invention, a capnograph may be used in detecting sleep apneas, either in conjunction with or separately from the pulse oximeter used in the techniques described above.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for diagnosis, comprising:
   receiving a signal associated with blood oxygen saturation of a patient during sleep;
   filtering the signal so as to eliminate signal components at frequencies equal to and greater than a respiratory frequency of the patient; and
   operating a computer for processing the filtered signal to determine a slope of the filtered signal, to distinguish Cheyne-Stokes breathing events from obstructive apnea events responsively to the slope, and to detect a pattern corresponding to multiple cycles of periodic breathing based on the distinguished Cheyne-Stokes breathing events.

2. The method according to claim 1, wherein processing the filtered signal comprises detecting the signal components that have a period greater than a minimum period of at least 30 sec.

3. The method according to claim 2, wherein the minimum period is at least 55 sec.

4. The method according to claim 1, and comprising determining a prognosis of heart failure (HF) in the patient based on the occurrences of the pattern of Cheyne-Stokes breathing.

5. The method according to claim 4, wherein determining the prognosis comprises predicting a probability of survival of the patient.

6. The method according to claim 4, wherein determining the prognosis comprises predicting a level of at least one marker, selected from a group of markers consisting of Brain Natriuretic Peptide (BNP) and N-terminal prohormone Brain Natriuretic Peptide (NT proBNP).

7. The method according to claim 4, wherein determining the prognosis comprises differentiating compensated from decompensated heart failure.

8. The method according to claim 4, wherein determining the prognosis comprises predicting a hospitalization of the patient.

9. The method according to claim 4, wherein determining the prognosis comprises providing an indication of a need for a change in treatment of the patient.

10. The method according to claim 4, wherein receiving the signal comprises receiving a photoplethysmograph signal from a sensor coupled to a body of a patient, wherein the method comprises processing the photoplethysmograph signal so as to identify a cardiac arrhythmia of the patient.

11. The method according to claim 10, wherein determining the prognosis comprises finding the prognosis responsively both to the occurrences of the pattern of Cheyne-Stokes breathing and to the cardiac arrhythmia.

12. The method according to claim 4, wherein determining the prognosis comprises assessing a duration of the occurrences of a pattern of Cheyne-Stokes breathing.

13. The method according to claim 12, and comprising treating the patient so as to reduce the duration of the occurrences of the pattern of Cheyne-Stokes breathing.

14. The method according to claim 12, wherein assessing the duration comprises finding a cumulative duration of the occurrences of the pattern of Cheyne-Stokes breathing.

15. The method according to claim 14, wherein finding the cumulative duration comprises classifying the patient in a high-mortality group if the cumulative duration exceeds a predetermined threshold.

16. The method according to claim 15, wherein the threshold is at least 45 minutes.

17. The method according to claim 1, wherein detecting the occurrences comprises identifying a Cheyne-Stokes breathing event when a duration of the multiple cycles is no less than a predetermined minimum duration.

18. The method according to claim 1, wherein detecting the occurrences comprises identifying a Cheyne-Stokes breathing event when a number of the multiple cycles is no less than a predetermined minimum number.

19. The method according to claim 18, wherein the minimum number is three.

20. The method according to claim 1, wherein the representative level of the blood oxygen saturation is one of a median saturation, a mean saturation, and a minimum saturation during the cycles.

21. The method according to claim 20, wherein the Cheyne-Stokes breathing event is identified when the representative level of the blood oxygen saturation is less than the blood oxygen saturation before the cycles by at least 2%.

22. The method according to claim 1, wherein determining the slope comprises finding a measure of the slope selected from a group of measures consisting of a median slope and a mean slope, and distinguishing the Cheyne-Stokes breathing events based on a maximal value of the measure of the slope in each of the cycles.

23. The method according to claim 22, wherein distinguishing the Cheyne-Stokes breathing events comprises classifying a breathing event as Cheyne-Stokes only when the maximal value of the measure is no greater than 0.7%/sec.

24. The method according to claim 1, and comprising screening the patient for heart failure based on the occurrences of the pattern of Cheyne-Stokes breathing.

25. The method according to claim 1, wherein receiving the signal comprises receiving a photoplethysmograph signal from a sensor coupled to a body of a patient, wherein the method comprises processing the photoplethysmograph signal so as to measure a heart rate of the patient.

26. The method according to claim 25, wherein processing the photoplethysmograph signal comprises identifying at least one premature ventricular contraction (PVC) in a heart rhythm of the patient.

27. The method according to claim 1, wherein receiving the signal comprises receiving a photoplethysmograph signal from a sensor coupled to a body of the patient, wherein the method comprises processing the photoplethysmograph signal so as to measure a vasomodulation in the body.

28. The method according to claim 1, wherein receiving the signal comprises receiving a photoplethysmograph signal from a sensor coupled to a body of the patient, wherein the method comprises processing the photoplethysmograph signal so as to measure a modulation of respiration by the patient.

29. The method according to claim 1, wherein receiving the signal comprises receiving a photoplethysmograph signal from a sensor on a finger of the patient, and wherein filtering the signal comprises digitizing and filtering the signal so as to generate data using processing circuitry in a control unit that is fastened to a forearm of the patient, and storing the data in a memory in the control unit.

30. The method according to claim 28, wherein processing the filtered signal comprises connecting the control unit to an external processor and uploading the data from the memory to the external processor for analysis, and wherein storing the data comprises receiving and recording the data in the control unit while the control unit is disconnected from the external processor.

31. The method according to claim 1, wherein receiving the signal comprises receiving a photoplethysmograph signal from a sensor implanted in a body of the patient.

32. Apparatus for diagnosis, comprising:
a sensor, which is configured to be coupled to a body of a patient during sleep and to output a signal associated with blood oxygen saturation in the body; and
a processor, which is coupled to filter the signal so as to eliminate signal components at frequencies equal to and greater than a respiratory frequency of the patient, and to process the filtered signal to determine a slope of the filtered signal, to distinguish Cheyne-Stokes breathing events from obstructive apnea events responsively to the slope, and to detect a pattern corresponding to multiple cycles of periodic breathing based on the distinguished Cheyne-Stokes breathing events.

33. The apparatus according to claim 32, wherein the processor is configured to detect the pattern by detecting the signal components that have a period greater than a minimum period of at least 30 sec.

34. The apparatus according to claim 33, wherein the minimum period is at least 55 sec.

35. The apparatus according to claim 32, wherein the processor is configured to determine a prognosis of heart failure (HF) in the patient based on the occurrences of the pattern of Cheyne-Stokes breathing.

36. The apparatus according to claim 35, wherein the prognosis is predictive of a probability of survival of the patient.

37. The apparatus according to claim 35, wherein the processor is configured to predict, based on the occurrences of the pattern of Cheyne-Stokes breathing, a level of at least one marker, selected from a group of markers consisting of Brain Natriuretic Peptide (BNP) and N-terminal prohormone Brain Natriuretic Peptide (NT proBNP).

38. The apparatus according to claim 35, wherein the processor is configured to differentiate compensated from decompensated heart failure based on the occurrences of the pattern of Cheyne-Stokes breathing.

39. The apparatus according to claim 35, wherein the processor is configured to predict a hospitalization of the patient based on the occurrences of the pattern of Cheyne-Stokes breathing.

40. The apparatus according to claim 35, wherein the processor is configured to provide an indication of a need for a change in treatment of the patient based on the occurrences of the pattern of Cheyne-Stokes breathing.

41. The apparatus according to claim 35, wherein the signal comprises a photoplethysmograph signal, and wherein the processor is configured to process the photoplethysmograph signal so as to identify a cardiac arrhythmia of the patient.

42. The apparatus according to claim 41, wherein the processor is configured to determine the prognosis responsively both to the occurrences of the pattern of Cheyne-Stokes breathing and to the cardiac arrhythmia.

43. The apparatus according to claim 35, wherein the processor is configured to determine the prognosis by assessing a duration of the occurrences of a pattern of Cheyne-Stokes breathing.

44. The apparatus according to claim 43, wherein the processor is configured to find a cumulative duration of the occurrences of the pattern of Cheyne-Stokes breathing.

45. The apparatus according to claim 44, wherein the processor is configured to classify the patient in a high-mortality group if the cumulative duration exceeds a predetermined threshold.

46. The apparatus according to claim 45, wherein the threshold is at least 45 minutes.

47. The apparatus according to claim 32, wherein the processor is configured to identify a Cheyne-Stokes breathing event when a duration of the multiple cycles is no less than a predetermined minimum duration.

48. The apparatus according to claim 32, wherein the processor is configured to identify a Cheyne-Stokes breathing event when a number of the multiple cycles is no less than a predetermined minimum number.

49. The apparatus according to claim 48, wherein the minimum number is three.

50. The apparatus according to claim 32, wherein the processor is configured to identify a Cheyne-Stokes breathing event when a representative level of the blood oxygen saturation during the cycles is less than the blood oxygen saturation before the cycles by at least a predetermined amount.

51. The apparatus according to claim 50, wherein the representative level of the blood oxygen saturation is one of a median saturation, a mean saturation, and a minimum saturation during the cycles.

52. The apparatus according to claim 51, wherein the Cheyne-Stokes breathing event is identified when the representative level of the blood oxygen saturation is less than the blood oxygen saturation before the cycles by at least 2%.

53. The apparatus according to claim 32, wherein the processor is configured to find a measure of the slope selected from a group of measures consisting of a median slope and a mean slope, and to distinguish the Cheyne-Stokes breathing events based on a maximal value of the measure of the slope in each of the cycles.

54. The apparatus according to claim 53, wherein the processor is configured to classify a breathing event as Cheyne-Stokes only when the maximal value of the measure is no greater than 0.7%/sec.

55. The apparatus according to claim 32, wherein the processor is configured to screen the patient for heart failure based on the occurrences of the pattern of Cheyne-Stokes breathing.

56. The apparatus according to claim 32, wherein the signal comprises a photoplethysmograph signal, and wherein the processor is configured to process the photoplethysmograph signal so as to measure a heart rate of the patient.

57. The apparatus according to claim 56, wherein the processor is configured to identify at least one premature ventricular contraction (PVC) in a heart rhythm of the patient.

58. The apparatus according to claim 32, wherein the signal comprises a photoplethysmograph signal, and wherein the processor is configured to process the photoplethysmograph signal so as to measure a vasomodulation in the body.

59. The apparatus according to claim 32, wherein the signal comprises a photoplethysmograph signal, and wherein the processor is configured to process the photoplethysmograph signal so as to measure a modulation of respiration by the patient.

60. The apparatus according to claim 32, wherein the sensor is configured to fit over a finger of the patient, and wherein the processor comprises a control unit, which is configured to be fastened to a forearm of the patient, and which is coupled to digitize and filter the signal so as to generate data indicative of the pattern, and which comprises a memory for storing the data.

61. The apparatus according to claim 60, wherein the control unit comprises an interface for connection to an external processor so as to upload the data from the memory to the external processor for analysis, and wherein the control unit is configured to receive and record the data while the control unit is disconnected from the external processor.

62. A computer software product, comprising:
a computer-readable medium in which program instructions are stored, which instructions, when read by a computer, cause the computer to receive a signal associated with blood oxygen saturation in a body or a patient, and to filter the signal so as to eliminate signal components at frequencies equal to and greater than a respiratory frequency of the patient, and to process the filtered signal to determine a slope of the filtered signal, to distinguish Cheyne-Stokes breathing events from obstructive apnea events responsively to the slope, and to detect a pattern corresponding to multiple cycles of periodic breathing based on the distinguished Cheyne-Stokes breathing events.

63. The product according to claim 62, wherein the instructions cause the computer to determine a prognosis of heart failure (HF) in the patient based on the occurrences of the pattern of Cheyne-Stokes breathing.

64. The product according to claim 63, wherein the prognosis is predictive of a probability of survival of the patient.

65. The product according to claim 63, wherein the signal comprises a photoplethysmograph signal, and wherein the instructions cause the computer to process the photoplethysmograph signal so as to identify a cardiac arrhythmia of the patient.

66. The product according to claim 65, wherein the instructions cause the computer to determine the prognosis responsively both to the occurrences of the pattern of Cheyne-Stokes breathing and to the cardiac arrhythmia.

67. The product according to claim 62, wherein the instructions cause the computer to identify a Cheyne-Stokes breathing event when a duration of the multiple cycles is no less than a predetermined minimum duration.

68. The product according to claim 62, wherein the instructions cause the computer to identify a Cheyne-Stokes breathing event when a representative level of the blood oxygen saturation during the cycles is less than the blood oxygen saturation before the cycles by at least a predetermined amount.

69. The product according to claim 62, wherein the signal comprises a photoplethysmograph signal, and wherein the instructions cause the computer to process the photoplethysmograph signal so as to measure a heart rate of the patient.

70. The product according to claim 69, wherein the instructions cause the computer to identify at least one premature ventricular contraction (PVC) in a heart rhythm of the patient.

71. The product according to claim 62, wherein the signal comprises a photoplethysmograph signal, and wherein the instructions cause the computer to process the photoplethysmograph signal so as to measure a vasomodulation in the body.

72. The product according to claim 62, wherein the signal comprises a photoplethysmograph signal, and wherein the instructions cause the computer to process the photoplethysmograph signal so as to measure a modulation of respiration by the patient.

73. A method for diagnosis, comprising:
- receiving a signal associated with blood oxygen saturation of a patient during sleep;
- filtering the signal so as to eliminate signal components at frequencies equal to and greater than a respiratory frequency of the patient;
- operating a computer for processing the filtered signal to distinguish Cheyne-Stokes breathing events from obstructive apnea events and to detect a pattern corresponding to multiple cycles of periodic breathing based on the distinguished Cheyne-Stokes breathing events.

74. The method of claim 73, further comprising finding a cumulative duration of the occurrences of the pattern of Cheyne-Stokes breathing, thereby assessing a duration of said occurrences of said pattern of Cheyne-Stokes breathing.

* * * * *